(12) United States Patent
Bender et al.

(10) Patent No.: US 7,335,216 B2
(45) Date of Patent: Feb. 26, 2008

(54) TOOL FOR CREATING AN OPENING IN TISSUE

(75) Inventors: Theodore M. Bender, San Francisco, CA (US); Brian R. DuBois, Redwood City, CA (US); Dan M. Pomeroy, Menlo Park, CA (US); Scott O. Chamness, Menlo Park, CA (US); Brendan M. Donohoe, San Francisco, CA (US)

(73) Assignee: Cardica, Inc., Redwood City, CA (US)

( * ) Notice: Subject to any disclaimer, the term of this patent is extended or adjusted under 35 U.S.C. 154(b) by 898 days.

(21) Appl. No.: 10/659,057

(22) Filed: Sep. 9, 2003

(65) Prior Publication Data
US 2005/0004591 A1    Jan. 6, 2005

Related U.S. Application Data

(63) Continuation-in-part of application No. 10/054,745, filed on Jan. 22, 2002.

(51) Int. Cl.
*A61B 17/32* (2006.01)
(52) U.S. Cl. .................. 606/167; 606/171; 606/180
(58) Field of Classification Search ................ 606/167, 606/169, 171, 180, 181
See application file for complete search history.

(56) References Cited

U.S. PATENT DOCUMENTS 2,850,007 A * 9/1958 Lingley ...................... 600/567

| 3,254,650 | A | 6/1966 | Collito |
| 3,519,187 | A | 7/1970 | Kapitanov et al. |
| 3,577,979 | A | 5/1971 | Gaast |
| 3,774,615 | A | 11/1973 | Lim et al. |
| 3,825,362 | A | 7/1974 | Hougen |
| 4,018,228 | A | 4/1977 | Goosen |

(Continued)

FOREIGN PATENT DOCUMENTS

DE        4041262        7/1991

(Continued)

OTHER PUBLICATIONS

Cardica PAS-Port Proximal Anastomosis System 510(k), Section VI.C., "Substantial Equivalence", and Attachment 7 (Unpublished).

(Continued)

*Primary Examiner*—Michael J. Hayes
*Assistant Examiner*—Michael G. Mendoza
(74) *Attorney, Agent, or Firm*—Brian A. Schar

(57) ABSTRACT

An piercing member is axially fixed to and positioned within a cutter, both of which are components of a stand-alone tool for creating an opening in the wall of a tubular tissue structure. The stand-alone tool includes an impulse source connected to the piercing member and to the cutter. An actuator is operationally connected to the impulse source, where the actuator causes the impulse source to release energy to and provide an impulse to the piercing member and the cutter. The tool may be configured to make multiple openings in the tissue of the same patient. Where the tool is configured to make multiple openings in the tissue of the same patient, the tool allows the piercing member and cutter to be moved back to an initial pre-deployment position after each use.

9 Claims, 15 Drawing Sheets

U.S. PATENT DOCUMENTS

| | | |
|---|---|---|
| 4,076,162 A | 2/1978 | Kapitanov et al. |
| 4,118,806 A | 10/1978 | Porier et al. |
| 4,214,587 A | 7/1980 | Sakura, Jr. |
| 4,216,776 A | 8/1980 | Downie et al. |
| 4,217,664 A | 8/1980 | Faso |
| 4,350,160 A | 9/1982 | Kolesov et al. |
| 4,352,358 A | 10/1982 | Angelchik |
| 4,366,819 A | 1/1983 | Kaster |
| 4,368,736 A | 1/1983 | Kaster |
| 4,503,568 A | 3/1985 | Madras |
| 4,523,592 A | 6/1985 | Daniel |
| 4,534,761 A | 8/1985 | Raible |
| 4,553,542 A | 11/1985 | Schenck et al. |
| 4,589,416 A | 5/1986 | Green |
| 4,593,693 A | 6/1986 | Schenck |
| 4,603,693 A | 8/1986 | Conta et al. |
| 4,607,637 A | 8/1986 | Berggren et al. |
| 4,624,255 A | 11/1986 | Schenck et al. |
| 4,624,257 A | 11/1986 | Berggren et al. |
| 4,657,019 A | 4/1987 | Walsh et al. |
| 4,665,906 A | 5/1987 | Jervis |
| 4,721,109 A | 1/1988 | Healey |
| 4,747,407 A | 5/1988 | Liu et al. |
| 4,752,024 A | 6/1988 | Green et al. |
| 4,873,991 A | 10/1989 | Skinner |
| 4,883,453 A | 11/1989 | Berry et al. |
| 4,907,591 A | 3/1990 | Vasconcellos et al. |
| 4,917,087 A | 4/1990 | Walsh et al. |
| 4,917,090 A | 4/1990 | Berggren et al. |
| 4,917,091 A | 4/1990 | Berggren et al. |
| 4,930,674 A | 6/1990 | Barak |
| 5,005,749 A | 4/1991 | Aranyi |
| 5,018,530 A * | 5/1991 | Rank et al. ............... 600/562 |
| 5,062,842 A | 11/1991 | Tiffany |
| 5,104,025 A | 4/1992 | Main et al. |
| 5,119,983 A | 6/1992 | Green et al. |
| 5,129,913 A | 7/1992 | Ruppert |
| 5,156,613 A | 10/1992 | Sawyer |
| 5,171,262 A | 12/1992 | MacGregor |
| 5,178,634 A | 1/1993 | Martinez |
| 5,187,796 A | 2/1993 | Wang et al. |
| 5,192,289 A | 3/1993 | Jessen |
| 5,192,294 A | 3/1993 | Blake, III |
| 5,193,731 A | 3/1993 | Aranyi |
| 5,205,459 A | 4/1993 | Brinkerhoff et al. |
| 5,217,474 A | 6/1993 | Zacca et al. |
| 5,221,281 A | 6/1993 | Klicek |
| 5,222,963 A | 6/1993 | Brinkerhoff et al. |
| 5,234,447 A | 8/1993 | Kaster et al. |
| 5,250,058 A | 10/1993 | Miller et al. |
| 5,250,060 A | 10/1993 | Carbo et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,290,298 A | 3/1994 | Rebuffat et al. |
| 5,292,053 A | 3/1994 | Bilotti et al. |
| 5,304,220 A | 4/1994 | Maginot |
| 5,314,435 A | 5/1994 | Green et al. |
| 5,314,468 A | 5/1994 | Martinez |
| 5,324,300 A | 6/1994 | Elias et al. |
| 5,333,773 A | 8/1994 | Main et al. |
| 5,336,233 A | 8/1994 | Chen |
| 5,344,059 A | 9/1994 | Green et al. |
| 5,350,104 A | 9/1994 | Main et al. |
| 5,354,302 A | 10/1994 | Ko |
| 5,364,389 A | 11/1994 | Anderson |
| 5,366,462 A | 11/1994 | Kaster et al. |
| 5,392,979 A | 2/1995 | Green et al. |
| 5,395,030 A | 3/1995 | Kuramoto et al. |
| 5,395,311 A | 3/1995 | Andrews |
| 5,403,338 A | 4/1995 | Milo |
| 5,423,330 A | 6/1995 | Lee |
| 5,423,796 A | 6/1995 | Shikhman et al. |
| 5,423,846 A | 6/1995 | Fischell |
| 5,443,497 A | 8/1995 | Venbrux |
| 5,447,514 A | 9/1995 | Gerry et al. |
| 5,454,825 A | 10/1995 | Van Leeuwen |
| 5,456,712 A | 10/1995 | Maginot |
| 5,456,714 A | 10/1995 | Owen |
| 5,462,062 A | 10/1995 | Rubinstein et al. |
| 5,464,449 A | 11/1995 | Ryan et al. |
| 5,465,895 A | 11/1995 | Knodel et al. |
| 5,470,320 A | 11/1995 | Tiefenbrun et al. |
| 5,478,354 A | 12/1995 | Tovey et al. |
| 5,488,958 A | 2/1996 | Topel et al. |
| 5,503,635 A | 4/1996 | Sauer et al. |
| 5,515,478 A | 5/1996 | Wang |
| 5,522,834 A | 6/1996 | Fonger et al. |
| 5,524,180 A | 6/1996 | Wang et al. |
| D372,310 S | 7/1996 | Hartnett |
| 5,533,661 A | 7/1996 | Main et al. |
| 5,540,677 A | 7/1996 | Sinofsky |
| 5,553,198 A | 9/1996 | Wang et al. |
| 5,556,405 A | 9/1996 | Lary |
| 5,558,667 A | 9/1996 | Yarborough et al. |
| 5,571,167 A | 11/1996 | Maginot |
| 5,591,187 A | 1/1997 | Dekel |
| 5,643,340 A | 7/1997 | Nunokawa |
| 5,645,520 A | 7/1997 | Nakamura et al. |
| 5,657,429 A | 8/1997 | Wang et al. |
| 5,669,918 A | 9/1997 | Balazs et al. |
| 5,669,934 A | 9/1997 | Sawyer |
| 5,676,670 A | 10/1997 | Kim |
| 5,690,662 A | 11/1997 | Chiu et al. |
| 5,693,088 A | 12/1997 | Lazarus |
| 5,695,504 A | 12/1997 | Gifford, III et al. |
| 5,702,412 A | 12/1997 | Popov et al. |
| 5,707,362 A | 1/1998 | Yoon |
| 5,707,380 A | 1/1998 | Hinchliffe et al. |
| 5,709,335 A | 1/1998 | Heck |
| 5,709,693 A | 1/1998 | Taylor |
| 5,725,544 A | 3/1998 | Rygaard |
| 5,725,553 A | 3/1998 | Moenning |
| 5,732,872 A | 3/1998 | Bolduc et al. |
| 5,754,741 A | 5/1998 | Wang et al. |
| 5,755,778 A | 5/1998 | Kleshinski |
| 5,762,458 A | 6/1998 | Wang et al. |
| 5,779,718 A | 7/1998 | Green et al. |
| 5,792,135 A | 8/1998 | Madhani et al. |
| 5,797,900 A | 8/1998 | Madhani et al. |
| 5,797,920 A | 8/1998 | Kim |
| 5,797,933 A | 8/1998 | Snow et al. |
| 5,799,661 A | 9/1998 | Boyd et al. |
| 5,799,857 A | 9/1998 | Robertson et al. |
| 5,807,377 A | 9/1998 | Madhani et al. |
| 5,814,073 A | 9/1998 | Bonutti |
| 5,815,640 A | 9/1998 | Wang et al. |
| 5,817,113 A | 10/1998 | Gifford, III et al. |
| 5,825,982 A | 10/1998 | Wright et al. |
| 5,827,316 A | 10/1998 | Young et al. |
| 5,833,698 A | 11/1998 | Hinchliffe et al. |
| 5,841,950 A | 11/1998 | Wang et al. |
| 5,855,583 A | 1/1999 | Wang et al. |
| 5,868,763 A | 2/1999 | Spence et al. |
| 5,868,764 A | 2/1999 | Rosengart |
| 5,871,495 A | 2/1999 | Mueller |
| 5,875,782 A | 3/1999 | Ferarri et al. |
| 5,878,193 A | 3/1999 | Wang et al. |
| 5,879,371 A | 3/1999 | Gardiner et al. |
| 5,881,943 A | 3/1999 | Heck et al. |
| 5,888,247 A | 3/1999 | Benetti |
| 5,893,369 A | 4/1999 | LeMole |
| 5,895,403 A | 4/1999 | Collinsworth |
| 5,895,404 A | 4/1999 | Ruiz |

| | | | | | | |
|---|---|---|---|---|---|---|
| 5,904,697 | A | 5/1999 | Gifford, III et al. | 6,248,117 | B1 | 6/2001 | Blatter |
| 5,907,664 | A | 5/1999 | Wang et al. | 6,253,768 | B1 | 7/2001 | Wilk |
| 5,910,121 | A | 6/1999 | Paolo et al. | 6,293,955 | B1 | 9/2001 | Houser et al. |
| 5,910,153 | A | 6/1999 | Mayenberger | 6,375,396 | B1 | 4/2002 | Fangmann et al. |
| 5,911,036 | A | 6/1999 | Wright et al. | 6,419,681 | B1 | 7/2002 | Vargas et al. |
| 5,915,616 | A | 6/1999 | Viola et al. | 6,485,496 | B1 | 11/2002 | Suyker et al. |
| 5,921,995 | A | 7/1999 | Kleshinski | 6,488,693 | B2 | 12/2002 | Gannoe et al. |
| 5,944,730 | A | 8/1999 | Nobles et al. | 6,673,088 | B1 | 1/2004 | Vargas et al. |
| 5,947,363 | A | 9/1999 | Bolduc et al. | 6,685,630 | B2 | 2/2004 | Sauer et al. |
| 5,957,363 | A | 9/1999 | Heck | 6,689,147 | B1 | 2/2004 | Koster, Jr. |
| 5,968,089 | A | 10/1999 | Krajicek | 2001/0000903 | A1 | 5/2001 | Heck et al. |
| 5,976,159 | A | 11/1999 | Bolduc et al. | 2001/0001122 | A1 | 5/2001 | Gifford, III et al. |
| 5,976,178 | A | 11/1999 | Goldsteen et al. | 2001/0001124 | A1 | 5/2001 | Mueller |
| 5,989,276 | A | 11/1999 | Houser et al. | 2001/0004697 | A1 | 6/2001 | Blatter et al. |
| 5,989,278 | A | 11/1999 | Mueller | 2001/0004698 | A1 | 6/2001 | Blatter et al. |
| 6,001,124 | A | 12/1999 | Bachinski | 2001/0016752 | A1 | 8/2001 | Berg et al. |
| 6,004,909 | A | 12/1999 | Lindman | 2001/0023354 | A1 | 9/2001 | Blatter et al. |
| 6,007,544 | A | 12/1999 | Kim | 2001/0029384 | A1 | 10/2001 | Nicholas et al. |
| 6,013,190 | A | 1/2000 | Berg et al. | 2001/0037139 | A1 | 11/2001 | Yencho et al. |
| 6,015,416 | A | 1/2000 | Stefanchik et al. | 2001/0047179 | A1 | 11/2001 | Gifford, III et al. |
| 6,022,367 | A | 2/2000 | Sherts | 2003/0065342 | A1 | 4/2003 | Nobis |
| 6,024,748 | A | 2/2000 | Manzo et al. | 2004/0073247 | A1 | 4/2004 | Loshakove |
| 6,025,015 | A | 2/2000 | Landry-Coltrain et al. | | | | |
| 6,030,370 | A | 2/2000 | Kupka et al. | | FOREIGN PATENT DOCUMENTS | | |
| 6,030,395 | A | 2/2000 | Nash et al. | DE | 297133357 | 11/1997 | |
| 6,036,699 | A | 3/2000 | Andreas et al. | EP | 0 517 252 | 12/1992 | |
| 6,036,700 | A | 3/2000 | Stefanchik et al. | EP | 0 701 800 | 3/1996 | |
| 6,036,702 | A | 3/2000 | Bachinski et al. | EP | 0 885 595 | 12/1998 | |
| 6,036,703 | A | 3/2000 | Evans et al. | EP | 0 938 870 | 9/1999 | |
| 6,036,704 | A | 3/2000 | Yoon | EP | 0 820 724 | 1/2000 | |
| 6,036,705 | A | 3/2000 | Nash et al. | EP | 0 820 725 | 1/2000 | |
| 6,036,710 | A | 3/2000 | McGarry et al. | EP | 0 913 125 | 7/2000 | |
| 6,050,472 | A | 4/2000 | Shibata | EP | 0 990 420 | 12/2000 | |
| 6,053,390 | A | 4/2000 | Green et al. | WO | 92/08513 | 5/1992 | |
| 6,056,762 | A | 5/2000 | Nash et al. | WO | 96/25886 | 8/1996 | |
| 6,066,144 | A | 5/2000 | Wolf et al. | WO | 97/25002 | 7/1997 | |
| 6,066,148 | A | 5/2000 | Rygaard | WO | 97/27898 | 8/1997 | |
| 6,068,637 | A | 5/2000 | Popov et al. | WO | 97/31575 | 9/1997 | |
| 6,074,416 | A | 6/2000 | Berg et al. | WO | 97/47261 | 12/1997 | |
| 6,080,167 | A | 6/2000 | Lyell | WO | 98/07399 | 2/1998 | |
| 6,080,173 | A | 6/2000 | Williamson, IV et al. | WO | 98/19608 | 5/1998 | |
| 6,080,175 | A | 6/2000 | Hogendijk | WO | 98/19618 | 5/1998 | |
| 6,080,176 | A | 6/2000 | Young | WO | 98/19625 | 5/1998 | |
| 6,083,234 | A | 7/2000 | Nicholas et al. | WO | 98/19629 | 5/1998 | |
| 6,083,238 | A | 7/2000 | Alexander, Jr. et al. | WO | 98/19630 | 5/1998 | |
| 6,110,188 | A | 8/2000 | Narciso, Jr. | WO | 98/19631 | 5/1998 | |
| 6,113,612 | A | 9/2000 | Swanson et al. | WO | 98/19632 | 5/1998 | |
| 6,117,148 | A | 9/2000 | Ravo et al. | WO | 98/19634 | 5/1998 | |
| 6,120,432 | A | 9/2000 | Sullivan et al. | WO | 98/19636 | 5/1998 | |
| 6,146,393 | A | 11/2000 | Wakabayashi | WO | 98/30153 | 7/1998 | |
| 6,149,681 | A | 11/2000 | Houser et al. | WO | 98/37814 | 9/1998 | |
| 6,152,937 | A | 11/2000 | Peterson et al. | WO | 98/42262 | 10/1998 | |
| 6,152,945 | A | 11/2000 | Bachinski et al. | WO | 98/47430 | 10/1998 | |
| 6,165,185 | A | 12/2000 | Shennib et al. | WO | 98/55027 | 12/1998 | |
| 6,167,889 | B1 | 1/2001 | Benetti | WO | 99/08603 | 2/1999 | |
| 6,171,319 | B1 | 1/2001 | Nobles et al. | WO | 99/17665 | 4/1999 | |
| 6,171,321 | B1 | 1/2001 | Gifford, III et al. | WO | 99/18887 | 4/1999 | |
| 6,176,413 | B1 | 1/2001 | Heck et al. | WO | 99/21491 | 5/1999 | |
| 6,176,864 | B1 | 1/2001 | Chapman | WO | 99/37218 | 7/1999 | |
| 6,176,867 | B1 | 1/2001 | Wright | WO | 99/38441 | 8/1999 | |
| 6,183,486 | B1 | 2/2001 | Snow et al. | WO | 99/38454 | 8/1999 | |
| 6,186,942 | B1 | 2/2001 | Sullivan et al. | WO | 99/40851 | 8/1999 | |
| 6,187,019 | B1 | 2/2001 | Stefanchik et al. | WO | 99/40868 | 8/1999 | |
| 6,187,020 | B1 | 2/2001 | Zegdi et al. | WO | 99/45848 | 9/1999 | |
| 6,190,396 | B1 | 2/2001 | Whitin et al. | WO | 99/52481 | 10/1999 | |
| 6,190,397 | B1 | 2/2001 | Spence et al. | WO | 99/62406 | 12/1999 | |
| 6,190,590 | B1 | 2/2001 | Randall et al. | WO | 99/62409 | 12/1999 | |
| 6,193,129 | B1 | 2/2001 | Bittner et al. | WO | 99/62415 | 12/1999 | |
| 6,193,734 | B1 | 2/2001 | Bolduc et al. | WO | 99/63910 | 12/1999 | |
| 6,206,912 | B1 | 3/2001 | Goldsteen et al. | WO | 99/65409 | 12/1999 | |
| 6,206,913 | B1 | 3/2001 | Yencho et al. | WO | 00/09040 | 2/2000 | |
| 6,235,054 | B1 | 5/2001 | Berg et al. | WO | 00/10486 | 3/2000 | |
| 6,241,742 | B1 | 6/2001 | Spence et al. | | | | |

| | | |
|---|---|---|
| WO | 00/12013 | 3/2000 |
| WO | 00/15144 | 3/2000 |
| WO | 00/15146 | 3/2000 |
| WO | 00/15147 | 3/2000 |
| WO | 00/15148 | 3/2000 |
| WO | 00/15149 | 3/2000 |
| WO | 00/27310 | 5/2000 |
| WO | 00/27311 | 5/2000 |
| WO | 00/27312 | 5/2000 |
| WO | 00/27313 | 5/2000 |
| WO | 00/33745 | 6/2000 |
| WO | 00/41633 | 7/2000 |
| WO | 00/53104 | 9/2000 |
| WO | 00/56223 | 9/2000 |
| WO | 00/56226 | 9/2000 |
| WO | 00/56227 | 9/2000 |
| WO | 00/56228 | 9/2000 |
| WO | 00/59380 | 10/2000 |
| WO | 00/66007 | 11/2000 |
| WO | 00/66009 | 11/2000 |
| WO | 00/69343 | 11/2000 |
| WO | 00/69346 | 11/2000 |
| WO | 00/69349 | 11/2000 |
| WO | 00/69364 | 11/2000 |
| WO | 00/72764 | 12/2000 |
| WO | 00/74579 | 12/2000 |
| WO | 00/76405 | 12/2000 |
| WO | 01/08601 | 2/2001 |
| WO | 01/12074 | 2/2001 |
| WO | 01/15607 | 3/2001 |
| WO | 01/17440 | 3/2001 |
| WO | 01/19257 | 3/2001 |
| WO | 01/19259 | 3/2001 |
| WO | 01/19284 | 3/2001 |
| WO | 01/34037 | 5/2001 |

OTHER PUBLICATIONS

Sales training brochure entitled "CorLink Automated Anastomosis Device" (2002).
"Notification of Transmittal of the International Search Report and the Written Opinion of the International Searching Authority", PCT/US04/28902 (WO 2005/023320), (May 25, 2007).
"International Search Report", PCT/US04/28902 (WO 2005/023320), (May 25, 2007).
"Written Opinion of the International Searching Authority", PCT/US04/28902 (WO 2005/023320), (May 25, 2007).

* cited by examiner

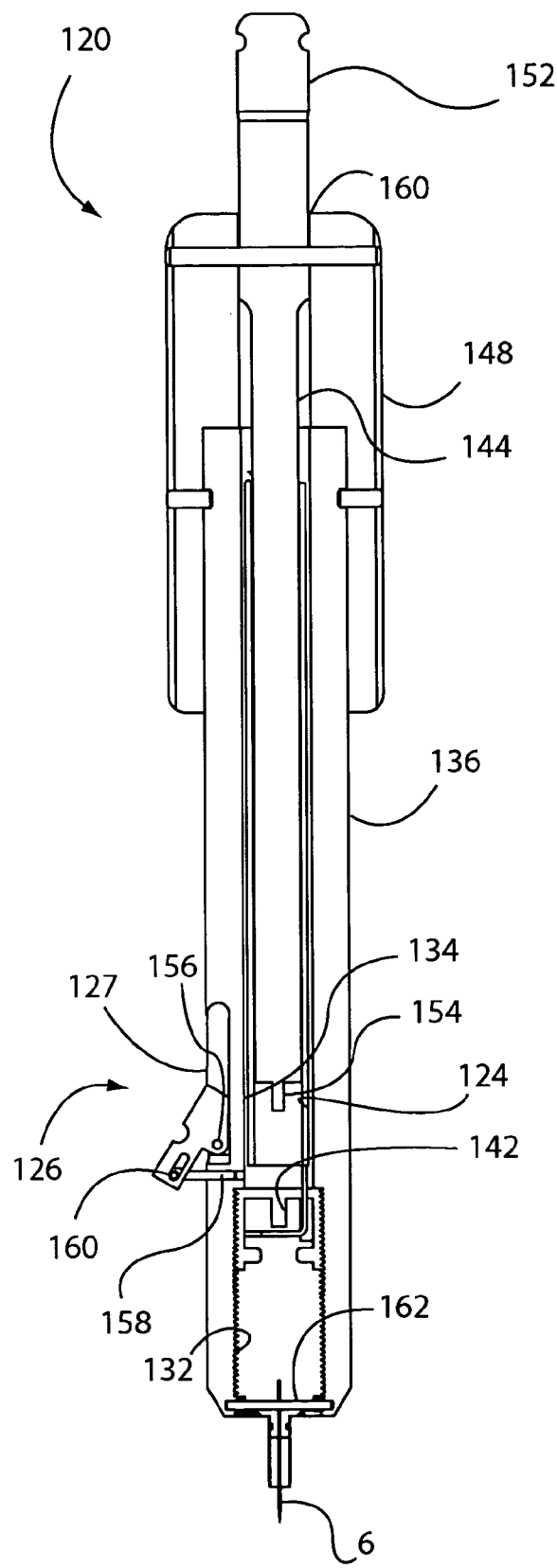
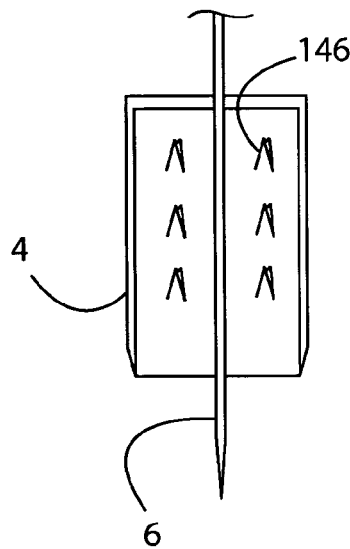
FIG. 18
FIG. 17

TOOL FOR CREATING AN OPENING IN TISSUE

This application is a continuation-in-part of U.S. patent application Ser. No. 10/054,745, filed Jan. 22, 2002.

FIELD OF THE INVENTION

The present invention relates generally to surgery, and more particularly to creating an opening in the wall of a tubular tissue structure such as a blood vessel.

BACKGROUND

Anastomosis is a procedure where two separate tubular or hollow organs are surgically grafted together to form an intercommunication between them. Vascular anastomosis involves creating an anastomosis between blood vessels to create or restore blood flow. The vascular anastomosis procedure is routinely performed during the treatment of a variety of conditions, including coronary artery disease (CAD), neurovascular disease, diseases of the great and peripheral vessels, organ transplantation, and traumatic injury. When a patient suffers from CAD, an occlusion or stenosis in a coronary artery restricts blood flow to the heart muscle. To treat CAD, the area where the occlusion occurs is bypassed to reroute blood flow by placing a graft vessel (in the form of a harvested artery or vein, prosthesis, allograft or xenograft) between two target vessels: the aorta or other supply of arterial blood, and the coronary artery. Placement of the graft vessel bypasses the blocked coronary artery, circumventing the occlusion and restoring adequate blood flow to the heart muscle. This treatment is known as a coronary artery bypass graft procedure (CABG). A CABG procedure can be performed on a stopped heart, where the patient has been placed on a heart-lung machine, or on a beating heart. Access to the thoracic cavity for a CABG procedure can be provided by sawing the sternum and opening the chest, or by creating one or more small openings in the thoracic cavity. Anastomosis may be performed by hand-suturing the graft vessels together or by utilizing an anastomosis device.

Regardless of the type of CABG procedure that is performed, or the type of anastomosis performed, an opening is made in the aorta or other artery at the proximal anastomosis site to allow blood to flow into the graft vessel. Typically, an incision is made in the aorta with a scalpel. A distal end of an aortic punch is inserted into the incision, then actuated to cut a larger opening in the aorta. While the combination of the scalpel and the aortic punch is commonly used to form an opening in the aorta, there are drawbacks. Between the time the incision is made and the time the aortic punch is used, it is difficult to maintain hemostasis. For example, the surgeon may place a finger over the incision after it is made. This is a problematic approach that does not provide reliable hemostasis during beating heart surgery, and has the potential to allow the location of the incision to become lost. Further, after the aortic punch creates an opening in the aorta, blood will flow out of that opening.

Other tools for creating an opening in a blood vessel wall utilize piercing members in conjunction with a cutter, where the piercing member and cutter are free to move relative to one another, and are actuated separately. The piercing member is generally deployed first, followed by the cutter. However, such an arrangement of the piercing member and the cutter can have difficulties in successfully creating a smooth opening in the blood vessel wall, and can have problems in retaining the tissue plug after it is removed from the blood vessel wall. Further, such an arrangement of the piercing member and cutter can be mechanically complex to implement.

SUMMARY

In one aspect of the invention, an auger is fixed relative to a cutter. The auger is positioned within the cutter, which may have a tubular structure. Because the auger and the cutter are fixed to one another, they rotate and advance together to penetrate the wall of a tubular vessel and cut tissue from it. The auger and the cutter are then retracted from the vessel wall. The auger retains the tissue within the cutter so that it can be removed from the vessel wall. The auger and the cutter thus create an opening in the vessel wall, without the need for a prior incision in that wall.

In another aspect of the invention, the auger and the cutter translate together but are free to rotate relative to one another. That is, the auger and the cutter are fixed with respect to translation, but not with respect to rotation. The auger and cutter are advanced together into the vessel wall, while one rotates and the other does not, or while both rotate at different rates or in different directions.

In another aspect of the invention, the cutter is vented to allow fluid such as air or blood to escape from it as the cutter and auger enter the wall of the tubular vessel. In this way, fluid does not become trapped within the cutter during operation, where it could create pressure that acts against the tissue of the vessel wall to oppose its entry into the cutter. The cutter may be vented by providing a longitudinal slot along at least a portion of its length, a single aperture at its proximal end, a plurality of apertures along its length, or in any other appropriate manner.

In another aspect of the invention, the cutter and auger are advanced into the wall of a tubular vessel through and ahead of an introducer having an internal diameter substantially the same as the outer diameter of the cutter. The distal end of the introducer enters the opening in the vessel wall as it is made, and remains in the opening after the auger and cutter are retracted, substantially sealing against the sides of the opening. The introducer, in combination with a seal housing or other plenum or structure connected to it, can thereby substantially maintain hemostasis both during and after creation of the opening.

In another aspect of the invention, the auger is part of an auger assembly. An actuator is attached to the auger assembly. The actuator is capable of rotational and translational motion. Because the cutter is fixed to the auger assembly, rotary and/or translational motion of the actuator causes corresponding motion of both the auger assembly and the cutter.

In another aspect of the invention, the auger assembly and cutter are rotated and advanced impulsively when stored energy is applied to them. The auger assembly and cutter are connected to an impulse source, such as a spring, via the actuator or other mechanism. The tissue of the tubular vessel may be strain rate sensitive, such that it is easier to cut when the cutting is performed rapidly than when it is performed slowly. By deploying the auger and cutter impulsively, they move rapidly to better cut strain rate sensitive tissue. In this way, the auger and cutter rapidly and accurately cut tissue from the wall of the tubular vessel.

In another aspect of the invention, the impulse source releases stored energy by rotating a first shaft. The first shaft is connected to a second shaft by gears, such that rotation of the first shaft causes rotation of the second shaft. The second shaft is threaded across a portion of its length, and that threaded portion is received in a threaded opening in a fixed structure. The threads are configured to translate the second shaft distally in response to the rotation of the first shaft. Thus, rotation of the first shaft is converted into both rotation and translation of a second shaft that is connected to the actuator, which in turn is connected to the auger assembly and/or the cutter.

In another aspect of the invention, a registration member is placed against the tubular vessel at an intended anastomosis site without substantially flattening it. The auger and cutter advance distally a fixed amount relative to the registration member. This fixed amount is selected to prevent the auger and cutter from translating completely across the diameter of the lumen of the tubular vessel and contacting its back wall.

In another aspect of the invention, rotational motion of a control assembly operatively connected to the auger assembly and the cutter controls the rotation and advancement of the auger assembly and cutter. This control assembly may include a cam cylinder having at least one cam path defined therein, a knob connected to the cam cylinder, and/or different or additional elements. The control assembly is configured to deploy the auger and cutter into tissue at a particular point in its rotational motion. The control assembly is operationally connected to an introducer tube and other associated components as well.

In another aspect of the invention, the cutter and a piercing member which may be any configuration of the auger are components of a stand-alone tool. Such a tool may be reusable, resposable or disposable. The stand-alone tool may be configured for making a single opening in the wall of a tubular tissue structure, or for making more than one opening in the wall of at least one tubular tissue structure of the same patient in the course of a surgical procedure. The stand-alone tool may be fabricated from materials that allow it to be sterilized and reused in a different patient at a later time. The stand-alone tool allows a user to make an opening of a standard size and shape in tissue with a single device.

In another aspect of the invention, the stand-alone tool includes an impulse source connected to the piercing member and to the cutter. The impulse source may be connected directly to the piercing member and the cutter, or may be connected indirectly to at least one of the piercing member and the cutter. An actuator is operationally connected to the impulse source, where the actuator causes the impulse source to release energy to and provide an impulse to the piercing member and the cutter. The actuator includes a trigger, which may be a lever, button, knob or any other suitable structure or mechanism. The actuator may be a single control or a combination of different controls that are simultaneously operated, or operated at different times. Advantageously, the actuator may be operated by a single motion of the user.

In another aspect of the invention, the cutter includes one or more tissue plug capture features. As an example of such a capture feature, a portion of the wall of the cutter is cut away, and cutter material adjacent to the cut is bent inward. For example, a V-shaped cut may be made in the cutter, where the open end of the V-shape is oriented substantially distally. The proximal end of the cutter material within the cut is bent inward slightly to form a capture feature. Such a capture feature allows the tissue plug to move proximally to or beyond its location on the cutter, but substantially prevents motion of the tissue plug distally past its location on the cutter, because the capture feature engages the tissue as it moves distally to arrest its motion.

In another aspect of the invention, the tool is configured to make multiple openings in the tissue of the same patient. Where the impulse source is or includes a mechanism or structure for storing energy, the tool allows for the addition of energy to the impulse source after each use. Alternately, the tool allows the impulse source to be changed out after each use. Alternately, the impulse source is configured to store enough energy to operate the piercing member and cutter for as many uses as expected for a particular patient, without the need for replenishment.

In another aspect of the invention, where the tool is configured to make multiple openings in the tissue of the same patient, the cutter may be long enough or otherwise configured with sufficient volume to hold multiple tissue plugs. As a result, the user need not remove each tissue plug from the cutter after making the corresponding opening. In this way, the duration of the overall surgical procedure may be reduced, which may be beneficial to the patient. Alternately, the tissue plug may be removed from the cutter automatically between uses.

In another aspect of the invention, where the tool is configured to make multiple openings in the tissue of the same patient, the tool is configured to allow the piercing member and cutter to be moved back to an initial pre-firing position after each use. For example, the piercing member and cutter may be fixed to a header located proximal to both said piercing member and said cutter, where that header is configured to rotate and advance as a result of contact with threads in the body of the tool. The header allows the piercing member and cutter to advance and rotate upon the application of an impulse thereto. The header and/or the body of the tool can also be manipulated after use to return the piercing member and the cutter to the pre-firing position.

BRIEF DESCRIPTION OF THE DRAWINGS

FIG. 17 is a side cross-section view of the assembly of FIG. 15 in a post-firing state.

FIG. 18 is a side cross-section detail view of an alternate auger and cutter forming part of the assembly of FIG. 15.

The use of the same reference symbols in different figures indicates similar or identical items.

DETAILED DESCRIPTION

Figure 1:
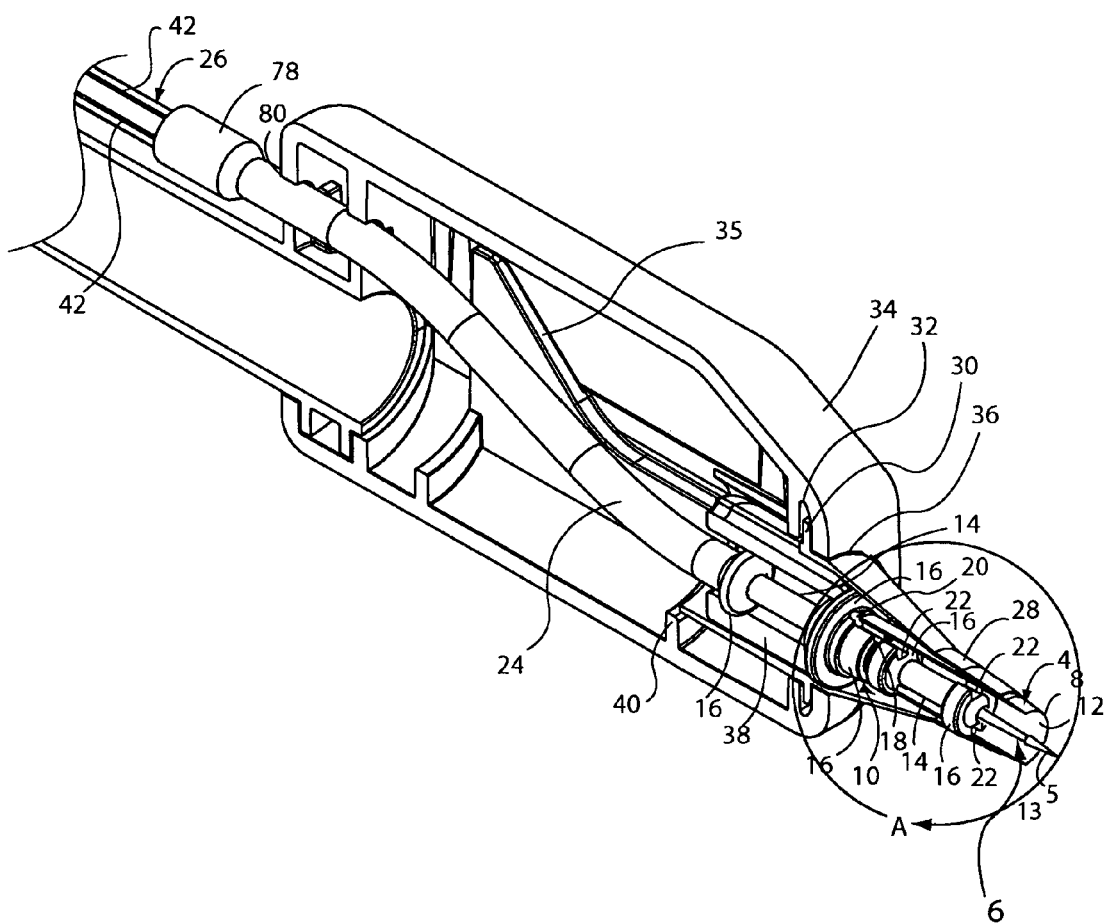
FIG. 1 is a cutaway view of the distal end of an assembly for creating an opening in the wall of a tubular vessel.
Figure 2:
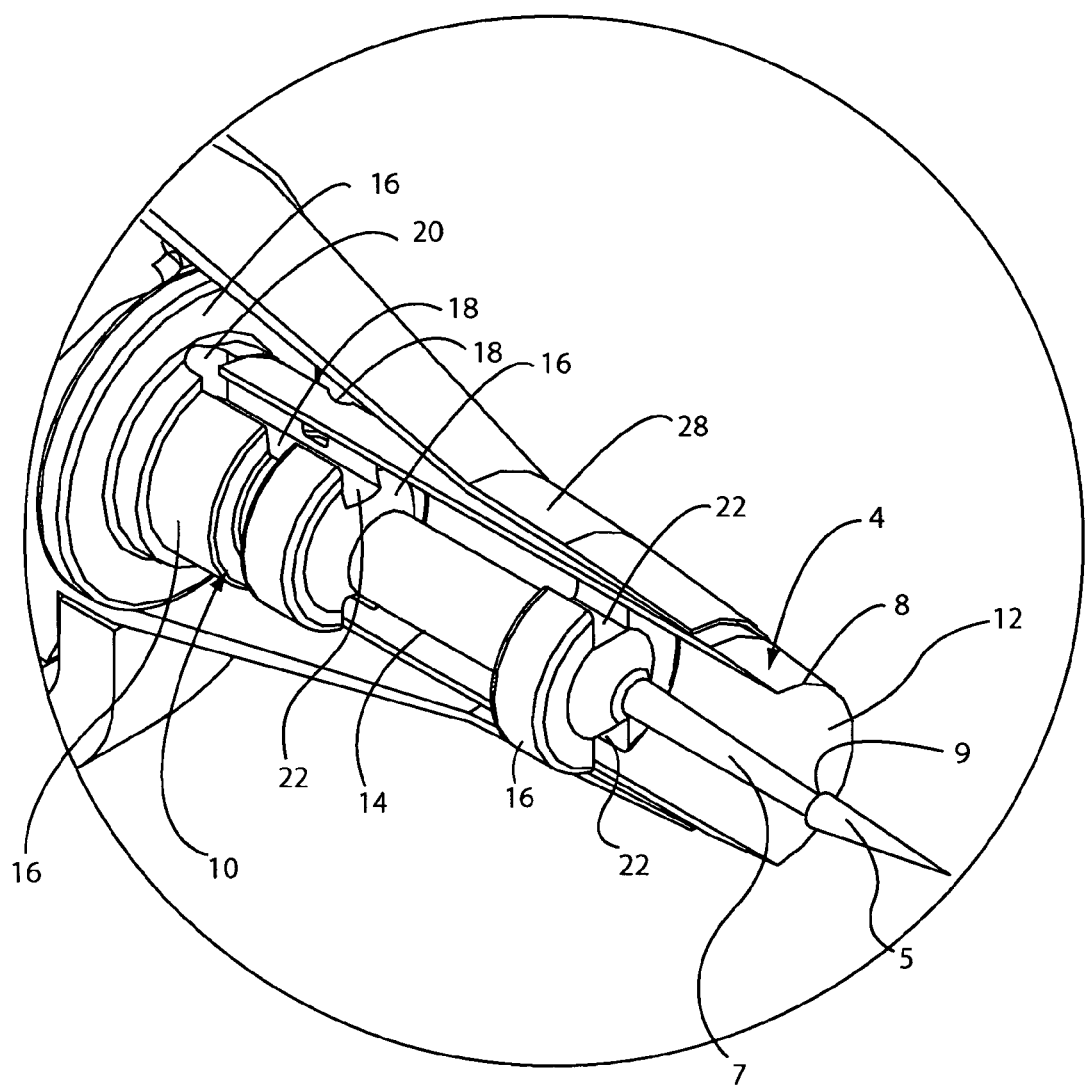
FIG. 2 is a detail view of the distal end of the assembly of FIG. 1.
Figure 3:
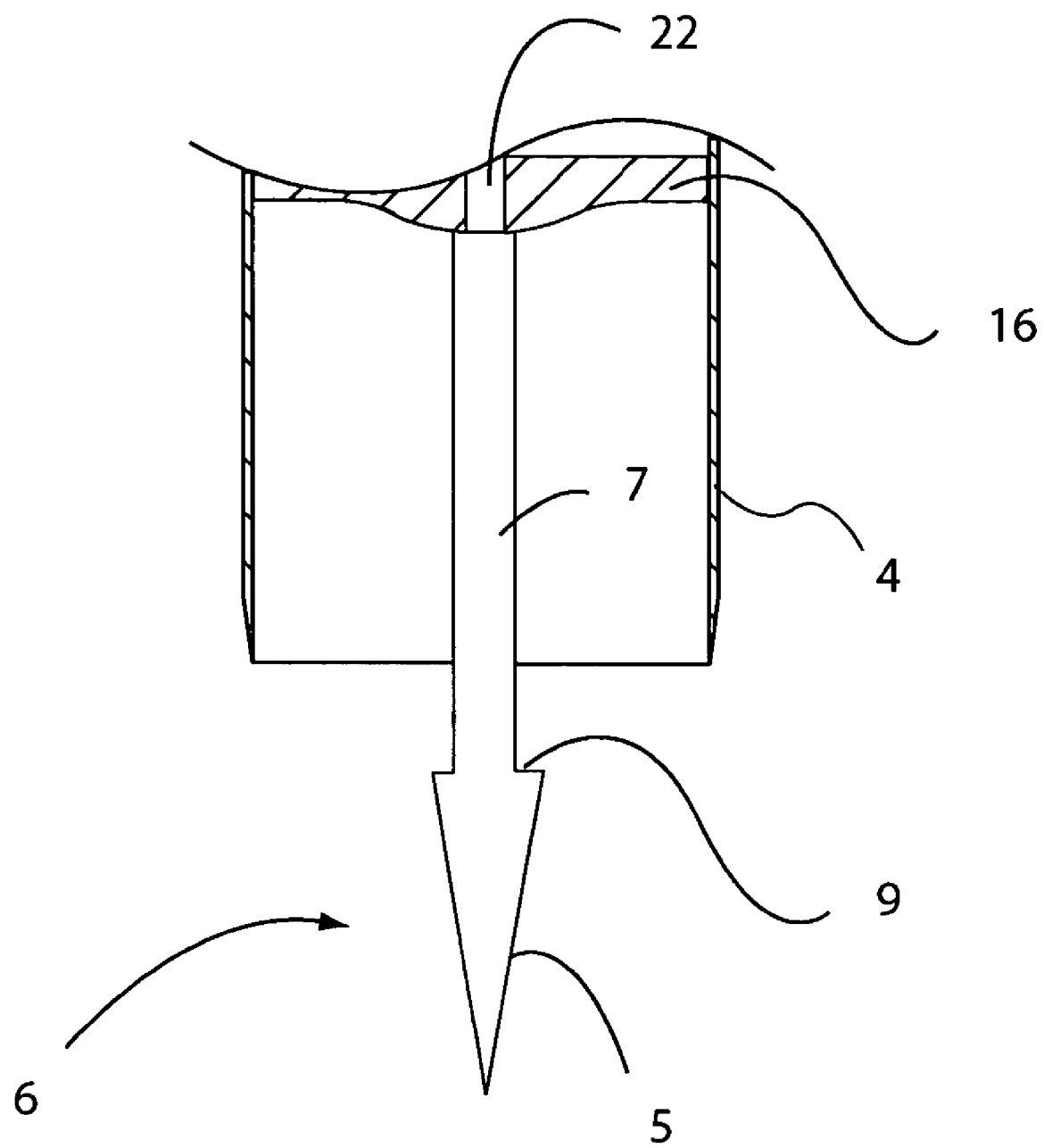
FIG. 3 is a cross-section detail view of an auger and cutter forming part of the assembly of FIGS. 1 and 2.

Referring to FIGS. 1-3, a cutter 4 is connected to an auger 6. The cutter 4 and auger 6 may be part of an integrated anastomosis tool. Alternately, the cutter 4 and auger 6 may be part of a stand-alone cutting tool, or a different tool or mechanism. The cutter 4 is constructed from a biocompatible metal, such as stainless steel, but a different biocompatible material may be used if desired. The distal end of the cutter 4 is sharpened to cut the wall of a tubular vessel, such as the aorta or other blood vessel. The cutter 4 is a hollow tubular structure with an open distal end. The distal end of the cutter 4 has a substantially circular shape, and the cutter 4 has a substantially circular cross-section along its length. However, the cutter 4 may take another shape, have a different cross section, or vary in cross section along its length. For example, the cutter 4 may take the shape of a tube having an open slit along its length. That is, the cutter 4 may form of the majority of a cylindrical surface, where the cutter 4 extends along, for example, 350° of the complete 360° perimeter of the cylinder. Alternately, the distal end of the cutter 4 may be angled relative to its longitudinal centerline, if desired. That is, the distal end of the cutter 4 may be coincident with a plane angled relative to the longitudinal centerline of the cutter 4. Alternately, the distal end of the cutter 4 may be shaped differently.

The cutter 4 has an inner surface 12 and an outer surface 8. The distal end of the cutter 4 is beveled for sharpness. The distal end of the cutter 4 may be beveled inward, such that the inner surface 12 contacts a vessel wall before the outer surface 8, or beveled outward, such that the inner surface 12 contacts a vessel wall after the outer surface 8. Alternately, the distal end of the cutter 4 may be beveled both inward and outward, such that a sharp edge is provided at a location between the inner surface 12 and outer surface 8 of the cutter 4. Alternately, less than the entire circumference of the distal end of the cutter 4 is sharpened. Alternately, the distal end of the cutter 4 is at least partially serrated.

The cutter 4 may have a smooth inner surface. Optionally, referring also to FIG. 18, the cutter 4 may include one or more tissue plug capture features 146 defined therein. As an example of such a capture feature 146, a portion of the wall of the cutter 4 is cut away, and cutter material adjacent to the cut is bent inward. For example, a V-shaped cut may be made in the cutter 4, where the open end of the V-shape is oriented substantially distally. The open end of the V-shape may be angled relative to the longitudinal direction, to facilitate capture of a tissue plug by the rotating cutter 4. The proximal end of the cutter material within the cut is bent inward slightly to form a capture feature 146. Such a capture feature 146 is a substantially triangular tab, with the point of the triangle oriented proximally. More than one capture feature 146 may be provided. If so, such capture features 146 may be linearly and/or longitudinally aligned with one another, unaligned with one another, arranged symmetrically, arranged asymmetrically, or otherwise positioned with respect to one another.

The auger assembly 10 is fixed to the cutter 4, and extends through its hollow center. In one embodiment, the auger assembly 10 extends through at least part of the hollow center of the cutter 4, and extends to a location proximal to the proximal end of the cutter 4. The auger assembly 10 is constructed from the same biocompatible metal as the cutter 4. Alternately, the auger assembly 10 may be constructed from a different biocompatible material. The auger assembly 10 may include a number of components. The auger 6 is one of these components, located at the distal end of the auger assembly 10. The auger 6 may be an integral part of the auger assembly 10, or instead may be a separate component that is connected to another portion of the auger assembly 10. Referring particularly to FIG. 3, the auger 6 is substantially coaxial with the cutter 4. The auger 6 includes a spike 5 at its distal end, and a shaft 7 extending proximally from the spike 5. The shaft 7 is substantially cylindrical. Alternately, the shaft 7 may be shaped differently. The spike 5 is tapered from its proximal end toward its distal end, and is substantially radially symmetrical. The distal end of the spike 5 is sharp to allow it to readily penetrate tissue, as described in greater detail below. The proximal end of the spike 5 is wider than the shaft 7, such that a ledge 9 is formed at the proximal end of the spike 5. The distal end of the spike 5 extends distal to the distal end of the cutter 4. Further, the spike 5 is positioned relative to the cutter 4 and is shaped such that the ledge 9 extends distally at least as far as the distal end of the cutter 4.

Alternately, the auger 6 and the cutter 4 are configured as described above, but are fixed to one another only axially; they are free to rotate with respect to one another. That is, the auger 6 and cutter 4 are configured to translate together at the same rate in the axial direction, but are free to rotate independently of one another. For example, the auger 6 may include a circumferential flange (not shown) held within a corresponding groove (not shown) in the cutter 4. The flange can rotate within the groove 4, and contact between the flange and the groove causes the auger 6 and cutter 4 to translate together. That is, the auger 6 and the cutter 4 are fixed axially, but independent rotationally. While the auger 6 and the cutter 4 are capable of rotating relative to one another, they need not do so, and may rotate together at the same rate if desired. Other mechanisms or structures may be used to configure the auger 6 and the cutter 4 to translate together axially while having the capability of rotating independently.

Figure 4:
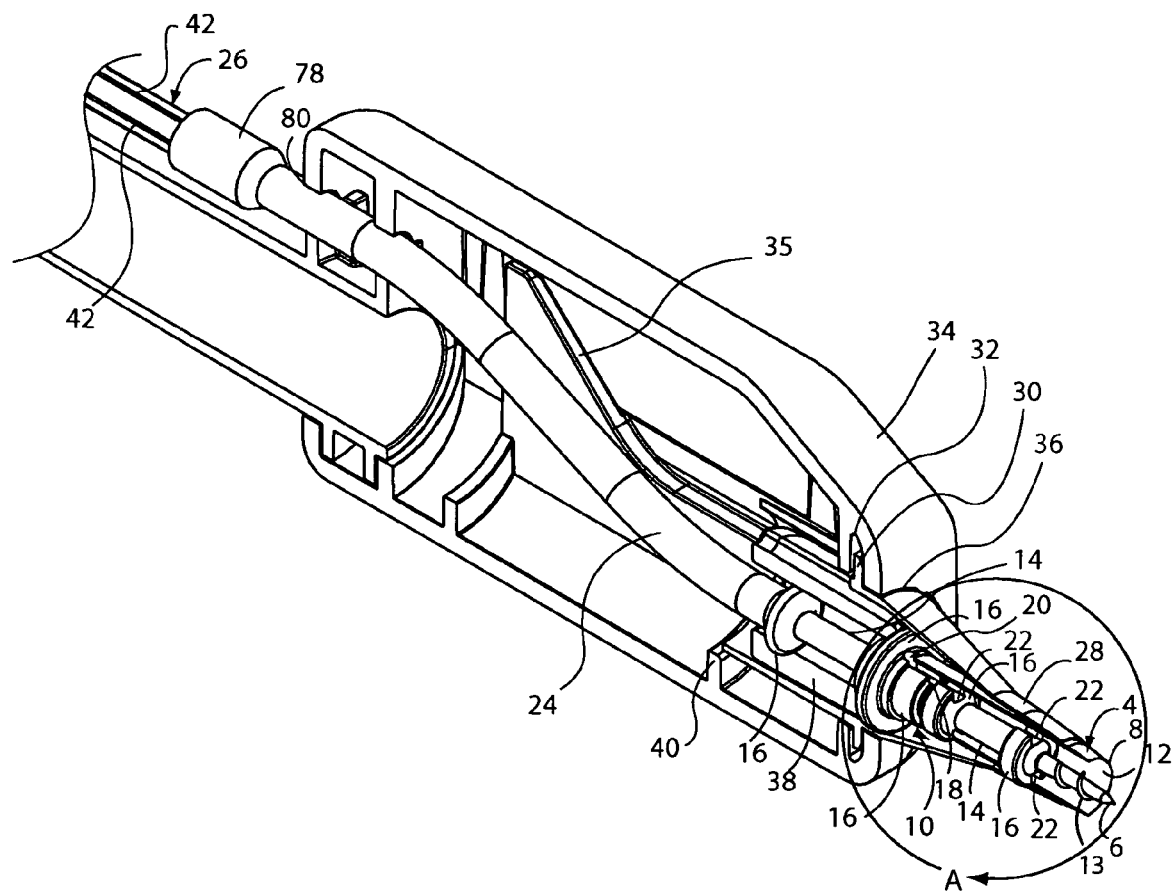
FIG. 4 is a cutaway view of the distal end of another embodiment of assembly for creating an opening in the wall of a tubular vessel.
Figure 5:
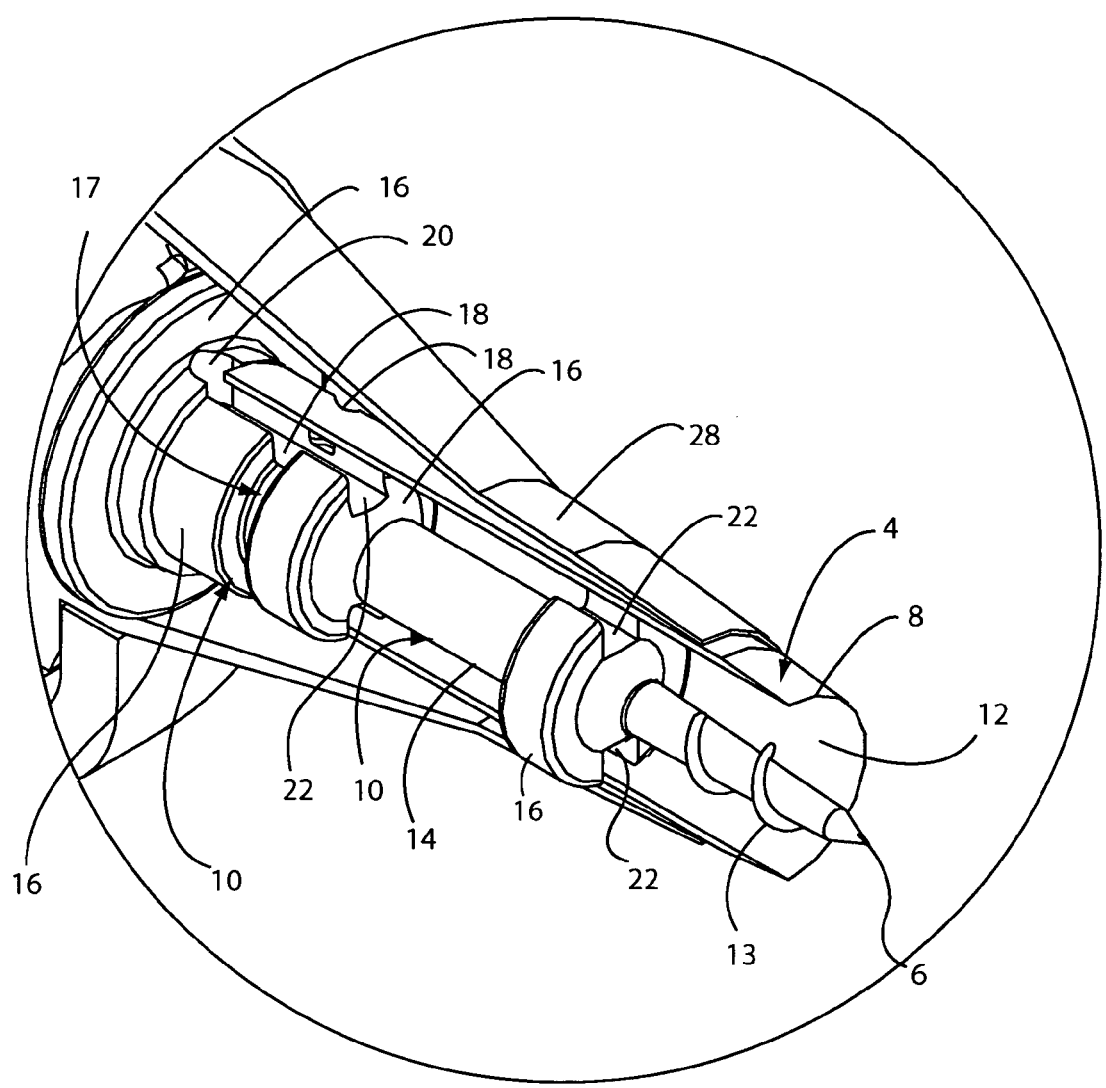
FIG. 5 is a detail view of the distal end of the assembly of FIG. 4.

Referring to FIGS. 4-5, another embodiment of the auger 6 is shown. The auger 6 has one or more flutes 13 defined on its outer surface. The flutes 13 have a pitch of substantially 16 threads per inch and a thread angle of substantially thirty-seven degrees. Alternately, a different pitch and/or thread angle may be used. In one embodiment, the auger 6 is tapered from its proximal end toward its distal end. The distal end of the auger 6 is sharp, to facilitate its entry into the wall of the tubular vessel, and extends to a location that is further in the distal direction than the distal end of the cutter 4. Alternately, a piercing member other than the auger 6 is axially fixed to the cutter 4, such as a barb, harpoon, lance, corkscrew or a needle without flutes.

The auger 6 may be a simple needle that does not include a spike 5 or one or more flutes 13. Such a needle may be solid or at least partially hollow. As an example, the needle may be simply a length of hypotube. As another example, the needle is a thin solid rod. The needle may be pointed or sharpened at its distal end. However, the needle may have a diameter small enough that its distal end is sharp enough to readily penetrated tissue as a consequence of its size. As with the other embodiments of the auger 6, the needle may be composed of any suitable biocompatible material. Advantageously, stainless steel is used to form the needle. However, any other suitable material or combination of materials may be used. Alternately, the auger 6 may be omitted altogether.

The auger assembly 10 includes a center rod 14 that is connected to the shaft 7 of the auger 6 and that is substantially coaxial with the cutter 4 and with the auger 6. Alternately, the center rod 14 may be positioned along a different axis. The shaft 7 may be formed as an integral part of the center rod 14. One or more centering flanges 16 are fixed to the center rod 14, extending outward radially from the center rod 14 to contact the cutter 4. One or more of the centering flanges 16 may be fixed to the cutter 4. The centering flanges 16 are utilized to position the center rod 14 within the cutter 4 along at a desired axis and to provide support and stiffness to the cutter 4. As described above, the centering flanges 16 may be utilized to center the center rod 14 within the cutter 4. In one embodiment, the centering flanges 16 are constructed as part of the center rod 14, thereby forming a unitary structure. However, the centering flanges 16 may be constructed separately from the center rod 14, then connected to the center rod 14, such as by adhesive or other fastening mechanism, structure or method. One or more centering flanges 16 may also be formed into or attached to the portion of the center rod 14 that extends proximal to the cutter 4. These centering flanges 16 may be utilized to position the center rod 14 relative to one or more other structures or mechanisms and/or to provide bearing surfaces for rotation of the auger assembly 10. The centering flanges 16 may have different thicknesses in the axial direction.

The cutter 4 is attached to the auger assembly 10 by dimpling the cutter 4 in one or more locations. One of the centering flanges 16 includes a groove 17 defined substantially circumferentially around it. The centering flange 16 that includes the groove 17 may be wider than one or more other centering flanges 16. Each dimple 18 is located within the groove 17. Each dimple 18 is formed by pressing the cutter 4 inward through the groove 17, causing that location on the cutter 4 to deform into a dimple 18. The dimple 18 expands into a portion of the groove 17, trapping the dimple 18 therein. The cutter 4 thus is fixed to the auger assembly 10, such that they rotate and translate together. Alternately, the cutter 4 includes one or more partially-circumferential ribs (not shown) extending inward from its inner surface 12. Each rib is crimped between two centering flanges 16, and is thereby trapped between them and fixed to them to fix the cutter 4 to the auger assembly 10. The auger assembly 10 may be connected to the cutter 4 using other or additional suitable mechanisms, structures or methods. Such a connection may be used where the auger 6 is fixed axially to, but free to rotate relative to, the cutter 4. For example, the auger assembly 10 and the cutter 4 may be molded or otherwise formed together as a single piece. As another example, the auger assembly 10 and the cutter 4 may be fixed together by adhesive. As another example, the auger assembly 10 and the cutter 4 may be fixed together by welding, or may be pinned or screwed together.

At least one vent 20 is defined in the auger assembly 10 at or proximal to the proximal end of the cutter 4. The vent 20 connects a space inside the cutter 4 with a space outside the cutter 4. Similarly, at least one slot 22 is defined through each centering flange 16. If a centering flange 16 is located adjacent to the proximal end of the cutter 4, the slot 22 in that centering flange 16 is aligned with the vent 20. The vent 20, in combination with the at least one slot 22 in each centering flange 16, provides a pathway for fluid such as air or blood to escape from the cutter 4 when the cutter 4 and auger 6 are deployed into the vessel wall. The cutter 4 is vented to prevent fluid from becoming trapped within the cutter 4, because the pressure of that trapped fluid could potentially prevent the cutter 4 from penetrating the vessel wall or other anatomical structure. Alternately, the vent 20 is a slot that extends substantially longitudinally through the cutter 4, along at least part of its length. This slot may be utilized instead of or in addition to a vent at or proximal to the proximal end of the cutter 4, as described above. The vent 20 may be curved and extend at least partially in the longitudinal direction; for example, it may be helical or sinusoidal. Alternately, more than one vent 20 is provided, where the vents 20 may be spaced longitudinally from one another. Other structures or mechanisms than the vent 20 and the slot 22 may be used to vent the cutter 4.

An actuator 24 is connected to the proximal end of the auger assembly 10. The center rod 14 extends to the proximal end of the auger assembly 10, and the actuator 24 connects to the center rod 14. Advantageously, the actuator 24 is a coil spring that is tightly wound, and the center rod 14 is threaded into the distal end of the spring. Alternately, the spring may be connected to the center rod 14 by adhesive, welding, soldering, compressive force or other methods or mechanisms. In this way, the spring provides flexibility and transmits translational and rotational force to the auger assembly 10. However, the actuator 24 may be any other structure or mechanism that is capable of transmitting translational and rotational forces to the auger assembly 10. Additionally, the actuator 24 need not be flexible if the auger 6 and cutter 4 are not moved off-axis, as is described in greater detail below. The actuator 24 is connected at its proximal end to the distal end of a first driveshaft 26.

At least a portion of the auger assembly 10 and the cutter 4 is positioned within a hollow introducer tip 28. The introducer tip 28 is a tapered element that is narrower at its distal end than at its proximal end. Alternately, the introducer tip 28 is not tapered. The introducer tip 28 has a substantially circular cross-section along its length. The introducer tip 28 is a radially and bilaterally symmetrical shell. Alternately, the introducer tip 28 can take a different shape, symmetry or form. The introducer tip 28 is composed of a biocompatible plastic, although a different material or combination of materials may be used. The inner diameter of the distal end of the introducer tip 28 is substantially the same as the outer diameter of the cutter 4, as measured at the distal end of the introducer tip 28. Further, the introducer tip 28 is substantially coaxial with the cutter 4. Thus, at the distal end of the introducer tip 28, the cutter 4 substantially seals against the introducer. As with the distal end of the cutter 4, the distal end of the introducer tip 28 may be beveled inward. Initially, the cutter 4 extends distally from the distal end of the introducer tip 28, and the distal end of the introducer tip 28 follows the cutter 4 into an opening cut in the wall of a tubular vessel, as is described in greater detail below. The introducer tip 28 may be splittable or expandable, if desired, such that the diameter of its distal end can be enlarged. Such enlargement may be useful in translating an anastomotic device through the introducer tip 28, or for other purposes.

The introducer tip 28 includes a circumferential flange 30 at or near its proximal end, where that flange 30 is held within a circumferential slot 32 in a seal housing 34 at or near its distal end. The introducer tip 28 thereby is secured to the seal housing 34. Alternately, the flange 30 is not circumferential, and the slot 32 in the seal housing 34 is correspondingly not circumferential. Alternately, the introducer tip 28 is secured to the seal housing 34 by a different structure, mechanism or method, such as by adhesive. The seal housing 34 is a substantially hollow structure into which the proximal end of the auger assembly 10 extends. The seal housing 34 includes an opening 36 at or near its distal end through which the introducer tip 28 and the auger assembly 10 extend. The cutter 4 extends proximally through the opening 36 in the seal housing 34. Alternately, the cutter 4 does not extend as far proximally as the opening 36 in the seal housing 34. The actuator 24 extends through the seal housing 34, and may extend out of an opening 40 at or near the proximal end of the seal housing 34. Alternately, the actuator 24 does not extend out of the seal housing.

The proximal end of the auger assembly 10 extends through the interior of a bushing 38. The bushing 38 is substantially cylindrical and has a substantially cylindrical opening therethrough. However, the bushing 38 and/or the opening through it may be shaped differently. The distal end of the bushing 38 contacts at least one centering flange 16 that is connected to the center rod 14. The distal end of the bushing 38 may be free to translate relative to that centering flange 16, where that centering flange 16 has a diameter larger than the passage through the bushing 38 such that the bushing 38 cannot advance distally past that centering flange 16. Alternately, the distal end of the bushing 38 contacts the inner surface of the introducer tip 28 instead of or in addition to at least one centering flange 16. The bushing 38 is restrained from rotation as the cutter 4 and auger assembly 10 rotate due to contact with at least one centering flange 16 and/or the introducer tip 28. However, registration features, stops or other structures or mechanisms may be used to restrain the bushing 38 from rotation. The bushing 38 may be tapered, such that the distal end of the bushing 38 contacts at least one centering flange 16, and another, wider location on the bushing 38 near the distal end of the bushing 38 contacts the inner surface of the introducer tip 28. The bushing 38 is supported by the introducer tip 28. The proximal end of the bushing 38 may contact a rib 40 or other structure within the seal housing 34. However, the proximal end of the bushing 38 is not fixed to the rib 40 or similar structure. Thus, the bushing 38 is free to translate proximally with respect to the introducer tip 28, but is restrained in its forward motion by contact with at least one centering flange 16 and/or introducer tip 28. One or more centering flanges 16 may be located within the bushing 38, and each centering flange 16 is connected to the center rod 14. However, the centering flanges 16 within the bushing 38 are free to rotate relative to the bushing 38. Thus, the auger assembly 10 may rotate relative to the bushing 38, and is supported and guided by the bushing 38 during this rotation.

A guide 35 is defined in or connected to the inner surface of the seal housing 34. The guide 35 may be a ramp, slot or other structure or mechanism. Advantageously, two guides 35 are provided, one on the inner surface of each side of the seal housing 34. For clarity, only one side of the seal housing 34 is shown. Because the seal housing 34 is substantially symmetrical, the guide 35 on the side of the seal housing 34 that is not shown is substantially symmetrical with the guide 35 shown. A guide follower (not shown) extends from the bushing 38 to contact or otherwise engage the corresponding guide 35. One guide follower is associated with each guide 35. The guides 35 are configured to guide the bushing 38, and with it the auger 6, cutter 4 and captured tissue away from the axis of the introducer tip 28 to a second axis spaced apart from the introducer axis, as is described in greater detail below. Thus, the location and orientation of the guides 35 on the inner surface of the seal housing 34 is dependent upon the location of the second axis.

Figures 6, 7:
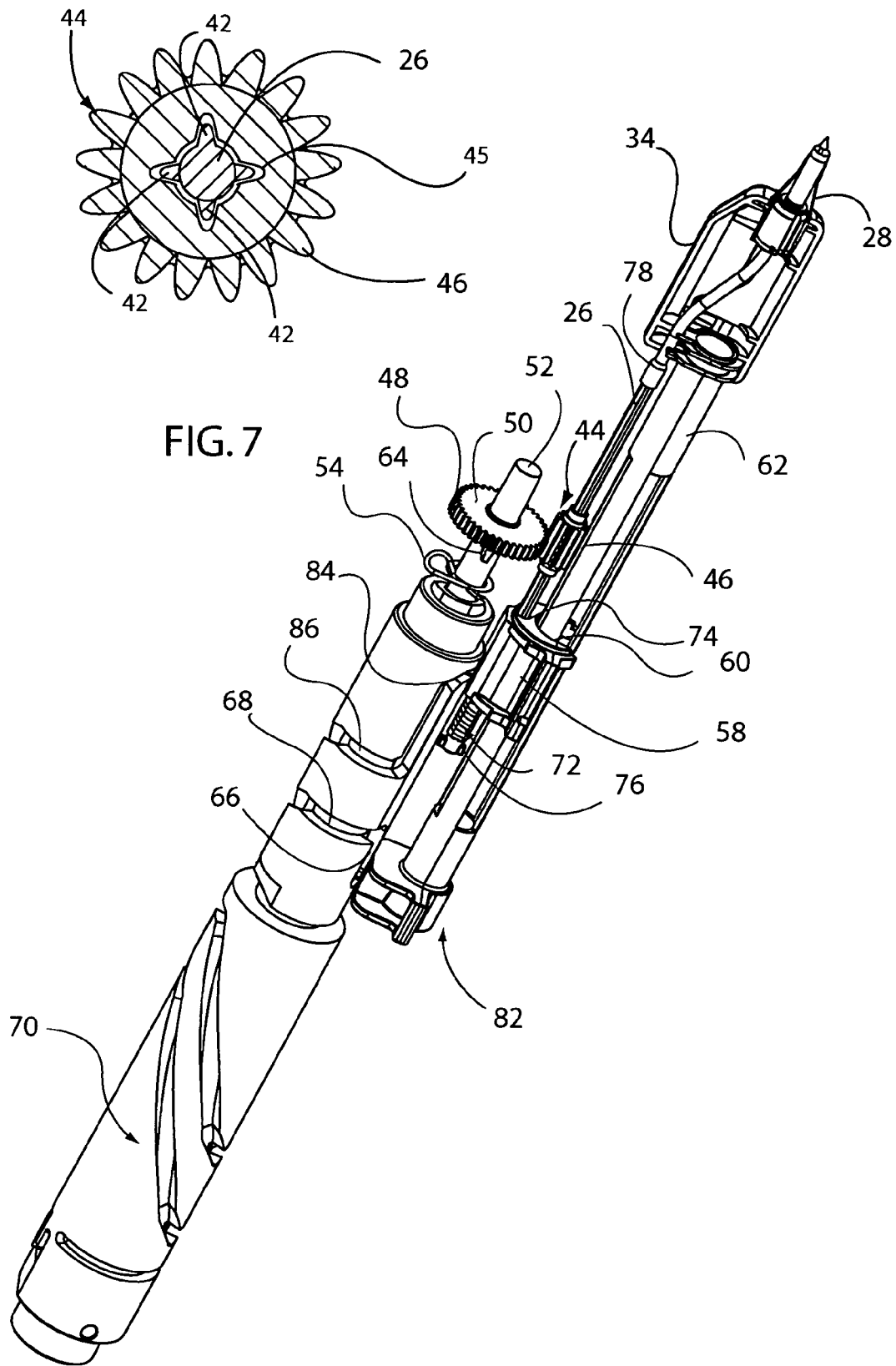
FIG. 6 is a perspective view of a drive mechanism for use with the assembly for creating an opening in the wall of a tubular vessel.
FIG. 7 is an end cross-section view of a first gear and a first driveshaft forming part of the drive mechanism of FIG. 6.

The auger assembly 10 and the cutter 4 can be actuated to rotate and to translate forward in any one of a number of ways. Referring also to FIG. 6, the distal end of a first driveshaft 26 is connected to the proximal end of the actuator 24. The connection between the first driveshaft 26 and the actuator 24 may be made inside or outside the seal housing 34. The first driveshaft 26 is substantially rigid, and has a number of ribs 42 aligned substantially axially along its surface, extending substantially radially outward. Alternately, the ribs 42 are aligned and/or extend differently. Four ribs 42 are spaced evenly around the circumference of the first driveshaft 26, but more or fewer ribs 42 may be utilized. The first driveshaft 26 is capable of axial translation relative to a first gear 44 that is substantially coaxial with the first driveshaft 26. The first gear 44 is mounted to a casing (not shown) or other structure, such that it is free to rotate about its axis but fixed in the axial direction and restrained against axial translation. Such mounting is standard in the art. The first gear 44 has a passage 45 therethrough, wherein a number of ribs (not shown) extend inward toward the rod 24 and are positioned between the ribs 42 on the first driveshaft 26. Contact between the ribs 42 and at least a portion of the surface of the passage 45 allows the first driveshaft 26 to translate axially relative to the first gear 44. Alternately, the first gear 44 and the first driveshaft 26 may be configured differently to allow rotary motion to be transmitted between the first driveshaft 26 and the first gear 44 while additionally allowing the first driveshaft 26 to translate axially relative to the first gear 44.

Figure 8:
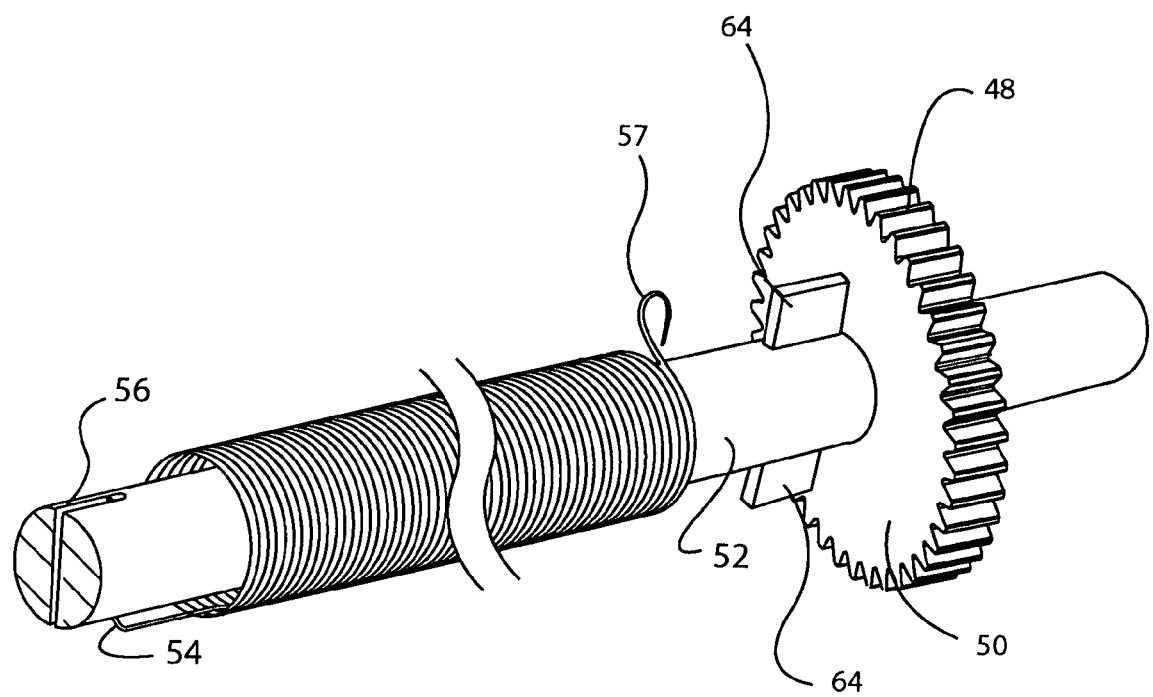
FIG. 8 is a perspective view of a second driveshaft forming part of the drive mechanism of FIG. 6.

Referring also to FIGS. 6-8, the first gear 44 has a number of teeth 46 aligned in a substantially axial direction and extending outward substantially radially. These teeth 46 interface with teeth 48 of a second gear 50, which correspondingly extend in a substantially axial direction. The second gear 50 has a diameter larger than that of the first gear 44, such that the gear ratio between the second gear 50 and the first gear 44 is larger than 1:1. Advantageously, the gear ratio is substantially 39:11. A different gear ratio may be used, if desired. The second gear 50 is mounted substantially coaxially to a second driveshaft 52 that is substantially parallel to the first driveshaft 26. Alternately, the second driveshaft 52 may be positioned in another orientation, and the teeth of the gears 44, 50 are constructed to interface at that orientation. Rotation of the second driveshaft 52 at a particular rate causes the first driveshaft 26 to rotate at a faster rate, due to the gear ratio of greater than 1:1 between the second gear 50 and the first gear 44.

The second driveshaft 52 may be driven by any mechanism or method. In one embodiment, the second driveshaft 52 is connected to an impulse source. A force that acts on a body for a short time but produces a large change in its linear or angular momentum is called an impulsive force. As used in this document, the term "impulse source" refers to a source of such an impulsive force. The impulse source is a torsional spring 54. However, the impulse source instead may be a different mechanism. The duration of the force generated by the spring 54 or other impulse source is substantially 0.05 seconds. However, the duration may be shorter or longer. Referring particularly to FIG. 8, the spring 54 surrounds at least a portion of the length of the second driveshaft 52. The proximal end of the spring 54 is fixed to a slot 56 in the second driveshaft 52. FIG. 8 shows a cross-section of the second driveshaft 52 for clarity in illustrating the connection between the spring 54 and the slot 56. The proximal end of the spring 54 is bent to fit into the slot 56, and is stiff enough and extends into the slot 56 far enough such that the contact between the proximal end of the spring 54 and the slot 56 holds the spring 54 in place. Alternately, the proximal end of the spring 54 is fixed to the second driveshaft 52 in another way. The distal end 57 of the spring 54 extends outward from the second driveshaft 52, and is fixed to a casing (not shown) or other structure relative to which the second driveshaft 52 rotates. Before the auger assembly 10 and cutter 4 are actuated, the spring 54 is wound up tightly, thereby storing a quantity of force in a torsioned state.

The impulse source may be different from the spring 54. For example, the impulse source may be a DC motor connected directly or via one or more gears to the second driveshaft 52. As another example, the impulse source may be a flow of biocompatible liquid such as water through an impeller or other mechanism connected to the second driveshaft 52. As another example, the impulse source is a magnetic field source coupled to the second driveshaft 52. A different impulse source than these exemplary ones may be used instead. In another embodiment, the impulse source is not used, and the auger assembly 10 and the cutter 4 are rotated non-impulsively, such as by hand.

One or more registration features 64 extend substantially radially outward from the second driveshaft 52 and/or the second gear 50. Each registration feature 64 is a tab. Alternately, the registration features 64 may be different structures than tabs. Where multiple registration features 64 are used, they are spaced evenly around the axis of the second driveshaft 52, but may be spaced differently if desired. Thus, where two registration features 64 are used, they are located on opposite sides of the second driveshaft 52, such that they fall substantially in the same plane. Alternately, the registration features 64 are not coplanar. If the registration features 64 are connected to the second gear 50, they are short enough such that they do not interfere with the operation of the second gear 50.

The registration features 64 are held by, or held relative to, the casing (not shown) or other structure or mechanism until rotation of the second driveshaft 52 is desired. Any appropriate structure or mechanism may be used to hold the registration features 64 relative to the casing. As one example, each registration feature 64 is positioned in a slot (not shown) defined by raised features on the inner surface of the casing, or against a ridge (not shown) extending inward from the casing toward the second driveshaft 52. The slots, ridges or other structures or mechanisms engage the registration feature or features 64 and restrain the second driveshaft 52 against rotation. Where the impulse source is the spring 54, the spring 54 biases the registration features 64 against the corresponding slots, ridges or other structures used to restrain the registration features 64. The registration features 64 are freed from the corresponding slots, ridges or other structures or mechanisms in order to allow rotation of the second driveshaft 52. For example, a slot holding a registration feature 64 is open at its distal end. Motion of the registration feature 64 distally frees it from the slot, allowing the second driveshaft 52 to rotate under the influence of the impulse source. As another example, a ridge holding a registration feature 64 extends axially. Motion of the registration feature 64 distally moves it beyond the ridge, allowing the second driveshaft 52 to rotate under the influence of the impulse source. Freeing the registration features 64 may be accomplished in a different manner, if desired.

As shown in FIG. 6, the second driveshaft 52 is in an initial position, in which the registration features 64 are restrained by slots, ridges, or other structures or mechanisms (not shown). This position may be referred to as the restrained position. After the second driveshaft 52 advances distally to free the registration features 64, the second driveshaft 52 is in a second position that may be referred to as the deployed position. The second gear 50 is fixed to the second driveshaft 52, such that the second gear 50 advances distally the same distance as the second driveshaft 52. The first gear 44 is at least as long as the distance that the second gear 50 advances, such that the first gear 44 is in mating contact with the second gear 50 throughout the entire distance that the second gear 50 translates.

The registration features 64 described above need not be used if the impulse source does not exert a force against the second driveshaft 52 until rotary motion of the second driveshaft is desired. For example, where the impulse source is a DC motor, the motor may be configured to exert a rotational force on the second driveshaft 52 only when rotary motion of the second driveshaft 52 is desired, and registration features 64 thus need not be provided to restrain the second driveshaft 52 against rotation in the initial position.

Figure 9:
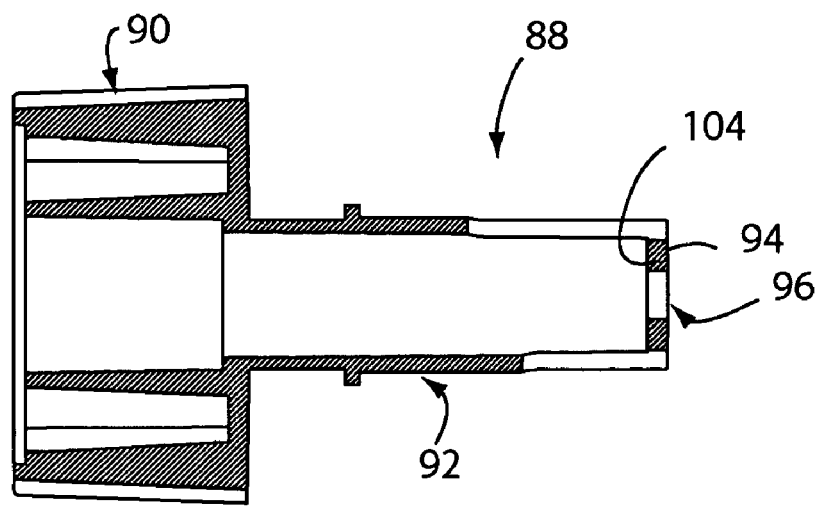
FIG. 9 is a cross-section view of a knob utilized to operate the drive mechanism of FIG. 6.
Figure 10:
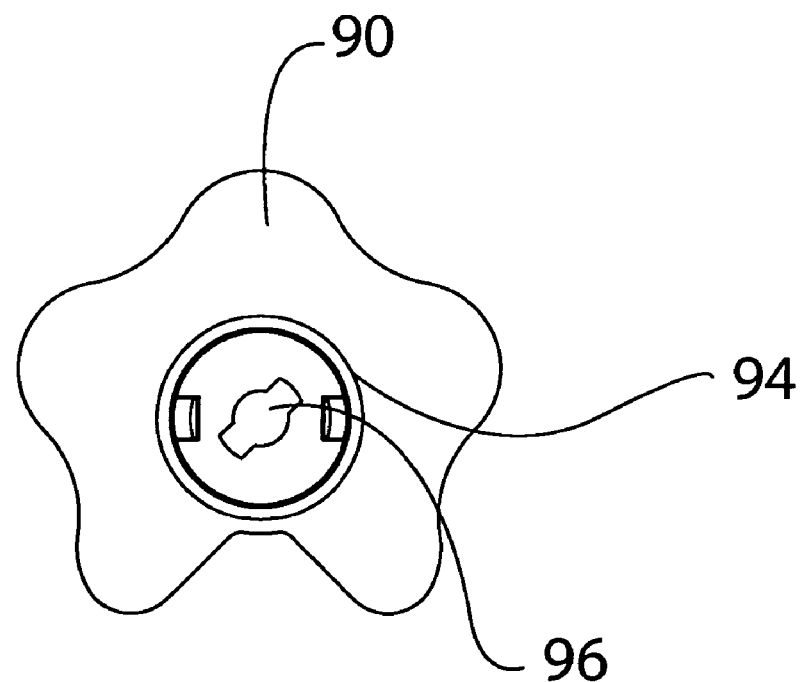
FIG. 10 is an end view of the knob of FIG. 9.
Figure 11:
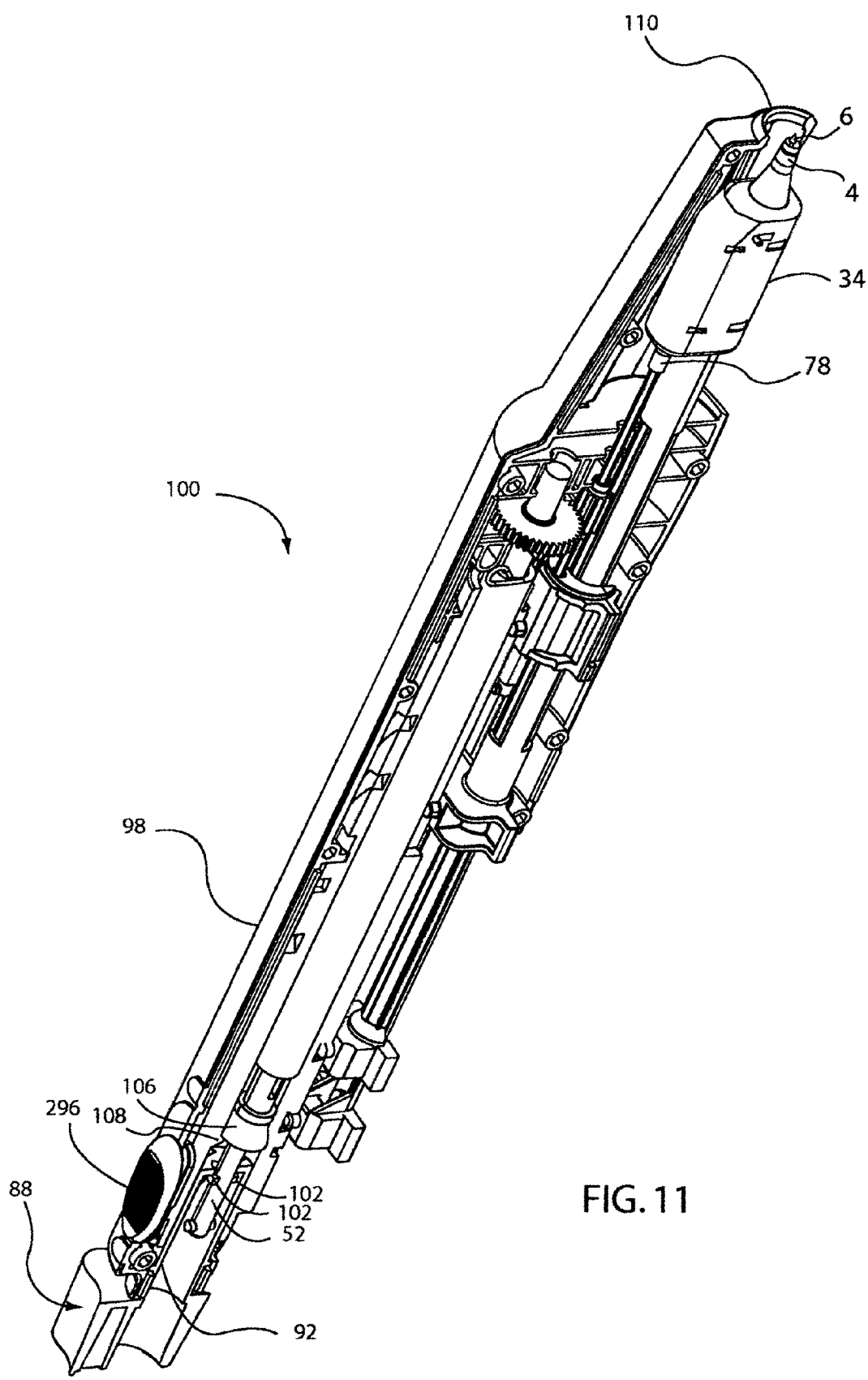
FIG. 11 is a cutaway view of an integrated anastomosis tool, where the tool is in an initial state.

Referring also to FIGS. 9-10, an exemplary embodiment of a knob 88 is shown, where the knob 88 is a component of an integrated anastomosis tool 100. The integrated anastomosis tool 100 is one example of a tool that utilizes and operates the auger 6 and cutter 4. The knob 88 includes a grip 90 and a hollow shaft 92. An endplate 94 is connected to the distal end of the shaft 92. The grip 90, shaft 92 and endplate 94 may be formed as a single piece, as by injection molding or another process. A slot 96 extends through the endplate 94. Referring also to FIG. 11, the shaft 92 extends into a casing 98. The casing 98 is substantially hollow, and one or more of the components described above in this document may be located within the casing 98. The casing 98 protects such components and assists in integrating them into a single integrated anastomosis tool 100. The slot 96 is shaped to allow the second driveshaft 52 to extend through it, such that the second driveshaft 52 extends distally into the shaft 92 of the knob 88.

Two stops 102 extend outward from opposite sides the second driveshaft 52. The stops 102 are shaped as substantially rectangular solids. Alternately, one or more stops 102 are shaped differently. Optionally, only one stop 102 may be used, or more than two stops 102 may be used, or the two stops 102 may be arranged differently on the second driveshaft 52. The stops 102 are initially positioned within the shaft 92 of the knob 88. The second driveshaft 52 is in the restrained position, as shown in FIG. 11, before deployment of the auger 6 and cutter 4. In this restrained position, the stops 102 are biased against the proximal surface 104 of the endplate 94, because the second driveshaft 52 is biased distally. A tapered compression spring 106 attached at its narrow end to the second driveshaft 52 performs the biasing, although a different structure or mechanism may be used. The narrow end of the compression spring 106 is positioned distal to the wider end of the compression spring 106. The wider end of the compression spring 106 presses against a circumferential ridge 108 defined on the casing 98. In the initial state, the compression spring 106 is compressed against the ridge 108, resulting in a distal biasing force. The compression spring 106 may be composed of rubber or a similar flexible substance. However, a different material may be used instead. The biasing force exerted by the compression spring 106 biases the stops 102 against with proximal surface 104 of the endplate 94 of the knob 88. The stops 102 are oriented such that they are not aligned with the slot 96 in the endplate 106, such that the second driveshaft 52 cannot pass through the slot 96 and thus is restrained against distal motion. Other structures or mechanisms than the compression spring 106 may be used to bias the second driveshaft 52, such as a coil spring or leaf spring.

Figure 12:
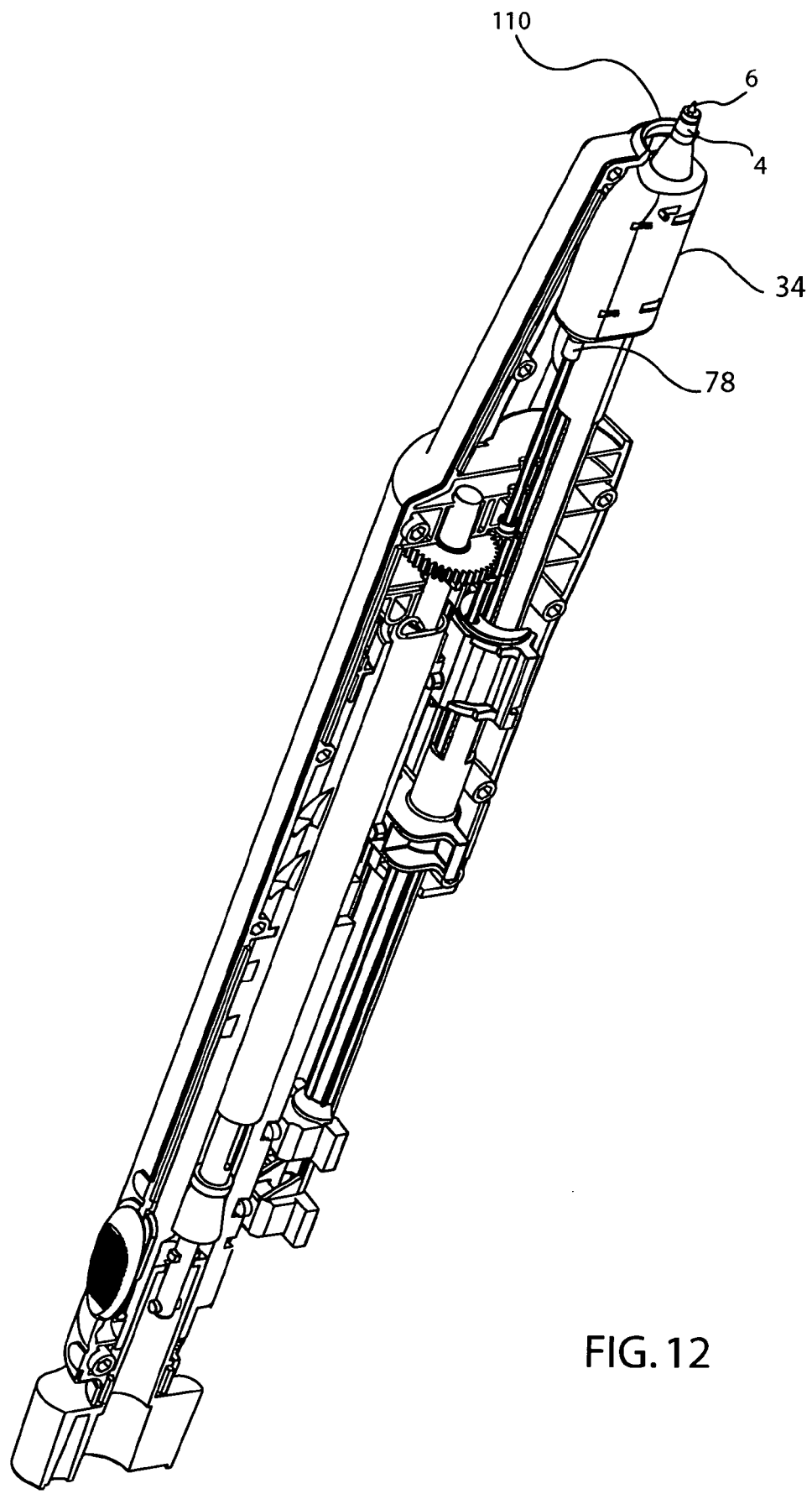
FIG. 12 is a cutaway view of the tool of FIG. 11 in a deployed state.

FIG. 12 shows the second driveshaft 52 in the deployed position, after deployment of the auger 6 and the cutter 4. The knob 88 has rotated, allowing the stops 102 to align with the slot 96 and slide through the slot 96 under the biasing influence of the compression spring 106. The compression spring 106 has moved to a less compressed state. The compression spring 106 may still exert a biasing force distally, but the distal end of the second driveshaft 52, the second gear 50, or another structure or mechanism contacts the casing 98 or another structure and prevents additional forward motion of the second driveshaft 52. The details of the motion of the second driveshaft 52 during operation are described in greater detail below.

Referring back to FIG. 6, the first driveshaft 26 is mounted to a carriage 58. The carriage 58 includes a concave surface 60 on its underside, where that concave surface 60 contacts an introducer tube 62. The introducer tube 62 is a hollow tube fixed to the seal housing 34, having a lumen that opens into the interior of the seal housing 34. That lumen may be substantially coaxial with the axis of the introducer tip 28. Alternately, the lumen of the introducer tube 62 may have an axis parallel to but not coaxial with, or not parallel to, the axis of the introducer tip 28. An anastomosis device (not shown) and vein graft (not shown) may be advanced through the lumen of the introducer tube 62, such that the anastomosis device can connect the vein graft to a target vessel after the auger 6 and cutter 4 have removed a tissue plug from the wall of the target vessel and created an opening therein.

The first driveshaft 26 includes a threaded portion 72 at or near the proximal end of the first driveshaft 26. Alternately, the threaded portion 72 of the first driveshaft 26 is located at another position on the first driveshaft 26. A passage 74 through the carriage 58 is correspondingly threaded to engage the threaded portion 72 of the first driveshaft 26. The threaded portion 72 of the first driveshaft 26 is configured to advance distally as the first driveshaft 26 rotates. Thus, rotary motion of the first driveshaft 26 is used to advance the first driveshaft 26, such that rotation of the second gear 50 is converted to both rotation and translation of the first driveshaft 26. Thus, the threaded portion 72 of the first driveshaft 26 is at least as long as the distance the first driveshaft 26 is to advance, and the corresponding threaded portion of the passage 74 through the carriage 58 can be any length that is capable of adequately supporting the first driveshaft 26 during its advancement. Alternately, the threaded portion 72 of the first driveshaft 26 is shorter than the distance the first driveshaft 26 is to advance, and the threaded portion of the passage 74 through the carriage 58 is at least as long as the distance the first driveshaft 26 is to advance. The threads of the threaded portion 72 of the first driveshaft 26 have a pitch of substantially 25 threads per inch. A different pitch may be utilized, if desired.

The first driveshaft 26 includes a head 76 at or near its proximal end. Alternately, the head 76 is located at a different position on the first driveshaft 26. The head 76 is a structure that is wider than the passage 74 through the carriage 58, such that contact between the head 76 and the carriage 58 stops the distal advancement of the first driveshaft 26. Thus, the head 76 limits the distal travel of the first driveshaft 26. Contact between the head 76 and the carriage 58 provides a positive stop after a particular amount of distal travel of the first driveshaft 26.

Alternately, the first driveshaft 26 does not include a threaded portion 72, and rotation of the second gear 50 causes the first driveshaft 26 to rotate but does not advance the first driveshaft 26 distally. In such an embodiment, a second impulse source (not shown) may be provided, and connected to the carriage 58 or first driveshaft 26 to advance the first driveshaft 26 substantially axially. The second impulse source may be a spring or other mechanism for storing energy and releasing it over a short interval of time. The second impulse source is coordinated with the first impulse source, such as the spring 54, such that both impulse sources produce an impulse at substantially the same time in order to produce rotational and translational motion of the auger assembly 10 and the cutter 4.

The timing, advancement and retraction of the auger assembly 10 and the cutter 4 can be controlled in a number of ways. In one embodiment, a cam cylinder 70 is used to control the advancement of the auger assembly 10 and the cutter 4. The knob 88 or other control structure is directly connected to and substantially coaxial with the cam cylinder 70, such that rotation of the knob 88 rotates the cam cylinder 70. The knob 88 instead may be operationally connected to the cam cylinder 70 via gearing or other mechanisms, such that the knob 88 and cam cylinder 70 can be oriented along different axes. Referring to FIG. 11, a first cam follower 66 extends from the introducer tube 62 into a first cam path 68 defined in the cam cylinder 70. The introducer tube 62 is restrained by the casing 98 and/or other structure or mechanism such that its motion is substantially linear along its axis. Consequently, the first cam follower 66 is restrained to move substantially linearly in a direction substantially parallel to the axis of the introducer tube 62. Rotation of the cam cylinder 70 causes the first cam path 68 to move relative to the first cam follower 66. The first cam follower 66 follows the first cam path 68, and thus can be caused to translate axially or be held stationary as the cam cylinder 70 is rotated. In the initial, restrained position, the first cam follower 66 is prevented from moving substantially distally or proximally by the first cam path 68, because the first cam path 68 is positioned relative to the first cam follower 66 substantially perpendicular to the direction in which the introducer tube 62 can translate, thereby substantially restraining the introducer tube 62 against translational motion. When the cam cylinder 70 is rotated and the first cam follower 66 encounters an segment of the first cam path 68 that extends in a direction having an axial component, the first cam follower 66 is free to translate a selected distance in the axial direction. Consequently, the introducer tube 62 that is connected to the first cam follower 66 is free to translate a selected distance in the axial direction, as is the seal housing 34 that is connected to the introducer tube 62.

Similarly, a second cam follower 84 extends from the carriage 58 into a second cam path 86 defined in the cam cylinder 70. The carriage 58 is restrained by the casing 98, introducer tube 62 and/or other structure or mechanism such that its motion is substantially linear in a direction substantially parallel to the axis of the introducer tube 62. In the initial, restrained position, as well as during translation of the second driveshaft 52, the second cam follower 84 is prevented from moving substantially distally or proximally by the second cam path 86. In that restrained position, the second cam path 86 is positioned relative to the second cam follower 84 substantially perpendicular to the direction in which the carriage 58 can translate, thereby substantially restraining the carriage 58 against translational motion. A segment of the second cam path 86 extends in a direction having an axial component. When the second cam follower 84 encounters such an segment of the second cam path 86, the second cam follower 84 is free to translate a selected distance in the axial direction, as is the carriage 58 that is connected to the second cam follower 84. The components connected to the carriage 58, such as the flexible shaft 24, the auger assembly 10 and the cutter 4, are also free to translate a selected distance in the axial direction. Thus, the motion of the auger assembly 10 and the cutter 4, as well as other components associated with them, can be controlled by rotation of the cam cylinder 70. That is, the cam paths 68, 86 allow translation of the associated followers 66, 84 when the cam paths 68, 86 are substantially parallel to the axis of the auger assembly 10, and substantially prevent motion of the associated followers 66, 84 when the cam paths are substantially perpendicular to the axis of the auger assembly 10. Alternately, only one of the cam followers 66, 84 is used to control the motion of the auger assembly 10 and the cutter 4.

Instead of a cam cylinder 70, a linear cam or a cam having another shape may be used to control the motion of the auger assembly 10 and the cutter 4. Further, in another embodiment, the motion of the auger assembly 10 and the cutter 4 is controlled by one or more different or additional mechanisms. For example, the auger assembly 10 and the cutter 4 may be connected to one or more DC motors or other powered mechanisms, where the motor is controlled by an integrated circuit or other computing device. By controlling the motor, the motion of the auger assembly 10 and the cutter 4 can be controlled.

An assembly 82 is advanced distally as a unit at least partially as far as the first driveshaft 26 advances. The assembly 82 includes the first driveshaft 26, the carriage 58, the seal housing 34, the introducer tube 62, the flexible shaft 24, the auger assembly 10, the cutter 4 and the introducer tip 28. Other components may be included in the assembly 82. Referring also to FIG. 1, a fitting 78 is connected to or formed into the first driveshaft 26 at or near its distal end. The fitting 78 is wider than the first driveshaft 26, and is substantially cylindrical. Alternately, the fitting 78 may be shaped differently. Optionally, the fitting 78 may be beveled or tapered at its distal end. The seal housing 34 may include a beveled or tapered area adjacent to the opening 80 corresponding to any beveling or tapering of the fitting 78. The fitting 78 has a diameter larger than the diameter of the opening 80 in the seal housing 34 through which the flexible shaft 24 extends. Optionally, the fitting 78 may be used to connect or assist in connecting the first driveshaft 26 and the actuator 24. The fitting 78 is positioned on the first driveshaft 26 at a location relative to the opening 80 such that the distal end of the fitting 78 engages the seal housing 34 next to the opening 80 as the first driveshaft 26 is advanced. Thus, the seal housing 34 is impelled forward along with the first driveshaft 26, due to contact between the fitting 78 and the seal housing 34. The initial distance between the fitting 78 and the seal housing 34 is related to the distance along which the assembly 82 is translated. As the seal housing 34 advances, the introducer tip 28 fixed to it is advanced into the opening created by the auger 6 and the cutter 4 in order to maintain hemostasis, as is described in greater detail below.

Alternately, the assembly 82 does not advance as a unit. Instead, the first driveshaft 26 advances the flexible shaft 24 distally, and the auger assembly 10 and cutter 4 advance distally as a result. The introducer tip 28 may be configured to advance into the opening created by the auger 6 and the cutter 4 at a later time, or may be configured to rest on the target vessel before the auger assembly 10 and the cutter 4 advance distally.

The operation of the auger assembly 10 and the cutter 4 of FIGS. 1-3 will now be described. Referring to FIGS. 11-12, a contact structure 110 is connected to or formed into the casing 98, and has an open perimeter. The perimeter of the contact structure 110 may take the shape of a circle with an arc removed, a U-shape, or other shape. The contact structure 110 is placed against the vessel to substantially stabilize its surface within the perimeter of the contact structure 110, such that the tubular vessel is not substantially flattened by the pressure applied to it via the contact structure 110. The cutter 4 and the auger assembly 10 are free to rotate and translate a fixed amount relative to the contact structure 110. Thus, the total translation of the cutter 4 and auger 6 relative to the contact structure 110 is known. The cutter 4 and auger 6 are placed on the vessel at a location where the diameter of the vessel is large enough to ensure that the cutter 4 and auger 6 do not encounter the rear wall of the vessel during their travel relative to the contact structure.

The distal end of the spike 5 of the auger 6 extends distally beyond the distal surface of the contact structure 110. Thus, as the contact structure 110 is moved toward against the vessel, the distal end of the spike 5 penetrates the vessel wall before the contact structure 110 contacts the vessel. The entry into the vessel wall of the spike 5 prior to actuation of the cutter 4 and the auger 6 facilitates tissue removal from the vessel wall. The vessel wall is intact before the spike 5 enters it, and no separate incision need be made in the vessel wall before the spike 5 encounters it.

Energy is applied impulsively to the auger assembly 10 and the cutter 4. The auger assembly 10 and the cutter 4 then begin to rotate, as they advance distally into the vessel wall. Rotation begins at substantially the same time as translation. However, rotation or translation may begin first. The auger 6 advances into the wall of the tubular vessel as the cutter 4 advances and cuts. The cutting action of the cutter 4 is both rotational and axial. By constructing the auger 6 and the cutter 4 to be substantially smooth and radially symmetrical, the rotary motion of these structures creates a substantially smooth and clean hole through the vessel wall. The tissue of the tubular vessel may be strain rate sensitive, such as the tissue of the aorta. Strain rate sensitive tissue is easier to cut when the cutting is performed rapidly than when it is performed slowly. By actuating the auger 6 and the cutter 4 impulsively, they move rapidly such that the cutter 4 can better cut strain rate sensitive tissue.

After the cutter 4 has penetrated the entire vessel wall, it has cut tissue from that vessel wall, and formed an opening corresponding to the former position of that tissue. The cutter 4 cuts a substantially cylindrical tissue plug from the vessel wall due to its tubular shape. The spike 5 is positioned relative to the cutter such that the tissue plug is held within the cutter 4 due to engagement with the ledge 9 after the tissue plug has been cut. That is, the ledge 9 has advanced completely through the vessel wall before the cutter 4, such that the tissue plug cut from the vessel wall is located proximally to the ledge 9 upon its creation. The ledge 9 is wide enough to reliably hold the tissue plug within the cutter 4. The shaft 7 extends axially through the tissue plug, such that contact between the shaft 7 and the tissue plug acts substantially to prevent radial motion of the tissue plug in the cutter 4. Where a capture feature or features 146 are utilized, they simply provide an additional degree of positive engagement between the cutter 4 and each tissue plug captured thereby.

The distal translation of the cutter 4 and auger 6 continues through a fixed distance greater than the thickness of the vessel wall, to ensure that the cutter 4 has completely penetrated the vessel wall. Thus, the cutter 4 and auger 6 may continue to advance for a short distance after the tissue plug has been cut out of the vessel wall having a particular wall thickness. The cutter 4 and auger 6 are then retracted through the introducer tip 28. As they are retracted, they retract the tissue plug, leaving an opening in the vessel wall.

The introducer tip 28 follows the cutter 4 and the auger 6 into the vessel wall, and remains in the opening thus formed, in order to provide hemostasis with regard to that opening. The introducer tip 28 is hollow, and has a diameter slightly larger than the opening. Thus, the introducer tip 28 fits snugly within that opening in order to prevent leakage of fluid from within the vessel between the introducer tip 28 and the opening. Fluid such as blood enters the seal housing 34 through the introducer tip 28, and the seal housing 34 maintains hemostasis with regard to the fluid in the vessel. Alternately, the introducer tip 28 is not used, such that fluid such as blood enters the seal housing 34 through the cutter 4. One or more tools deployed through the introducer tube 62 have an outer diameter slightly smaller than the inner diameter of the introducer tube 62, such that the close fit between the introducer tube 62 and the tools deployed within it substantially provides hemostasis and prevents leakage from the seal housing 34. Alternately, a valve or seal (not shown) may be provided between the introducer tube 62 and the seal housing 34 to substantially prevent blood from entering the lumen of the introducer tube 62. Thus, the seal housing 34 maintains hemostasis in conjunction with the introducer tip 28 and/or the cutter 4. The introducer tip 28 may be omitted where the auger 6 and cutter 4 are part of an independent cutting tool rather than an integrated anastomosis tool or other integrated tool.

The auger assembly 10 and cutter 4 work similarly where the auger 6 is configured as shown in FIGS. 4-5. The contact structure 110 is placed against the vessel wall. The auger 6 and the cutter 4 initially are located proximal to the distal surface of the contact structure 110 and do not contact the vessel wall. As described above, energy is applied impulsively to the auger assembly 10 and the cutter 4, which begin to rotate and also begin to translate toward the wall of a tubular vessel. Thus, the auger assembly 10 and the cutter 4 each have both angular and linear momentum when they encounter the wall of the tubular vessel. The auger 6 encounters the vessel wall before the cutter 4, because the tip of the auger 6 extends distally beyond the distal end of the cutter 4. The vessel wall is intact before the auger 6 encounters it. That is, no separate incision need be made in the wall of the tubular vessel before the auger 6 and cutter 4 encounter it.

Figure 13:
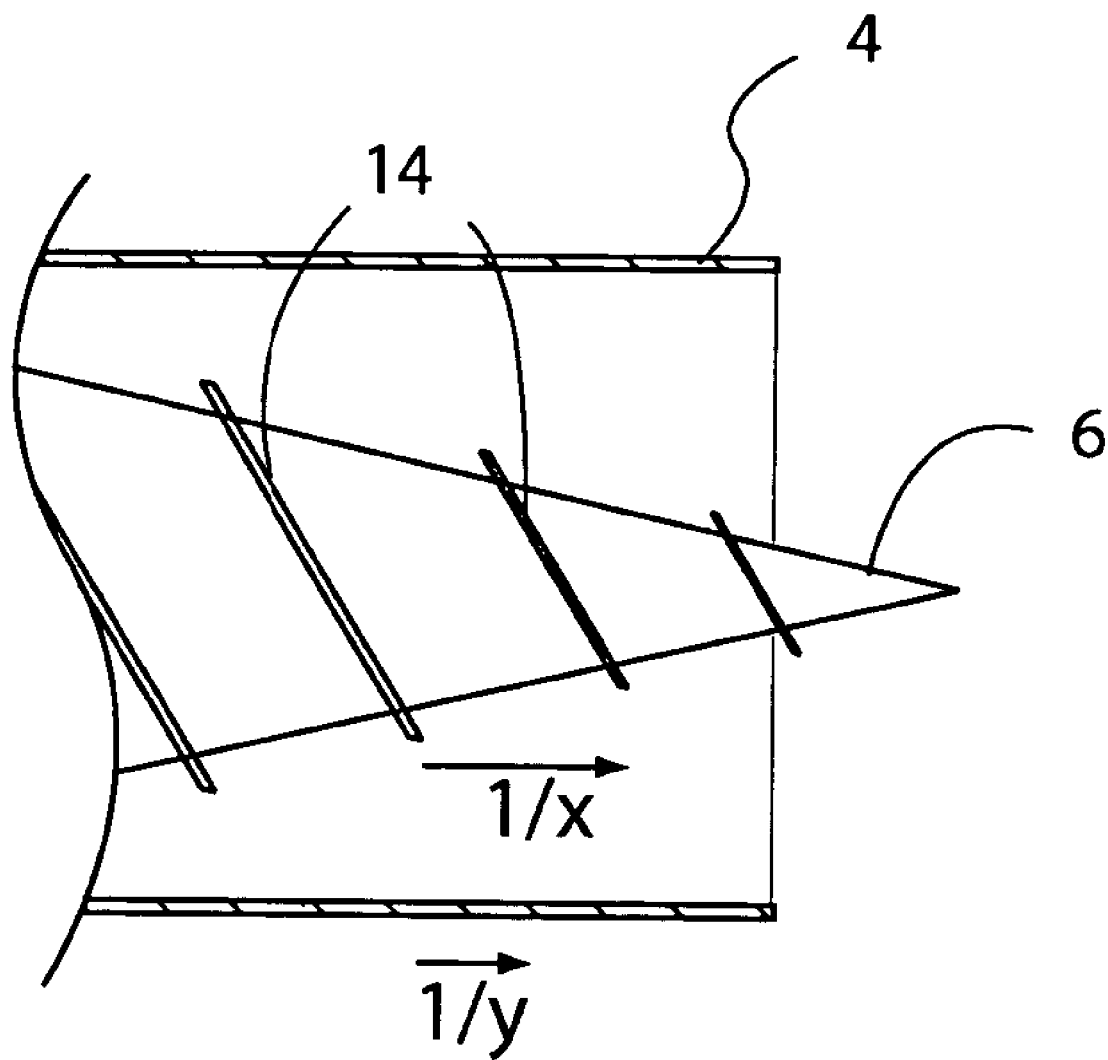
FIG. 13 is a detail view of the auger and cutter of FIGS. 4-5.

Referring also to FIG. 13, half of the cutter 6 is cut away in order to illustrate the auger 6 more completely. The auger flutes 13 have a pitch X, meaning that the flutes 13 cause the auger 6 to penetrate a distance 1/X into the wall of the tubular vessel for each revolution of the auger 6. Thus, at a pitch of 16 threads per inch, the auger 6 advances into the tubular vessel 1/16 inch each revolution of the auger 6. Similarly, the threads of the threaded portion 72 of the first driveshaft 26 have a pitch Y. Thus, at a pitch of 25 threads per inch, the auger 6 and the cutter 4 translate distally 1/25 inch each revolution of the first driveshaft 26. The auger assembly 10 and the first driveshaft 26 are fixed to one another and thus rotate at the same rate. The distance 1/X is greater than the distance 1/Y. Both distances are measured relative to the contact structure 110, which provides a point of reference as to the motion of the auger 6 and the cutter 4. The auger 6 advances into the wall of the tubular vessel faster than the cutter 4, even though the auger 6 and cutter 4 are impelled distally at the same rate. As a result, the auger 6 pulls the wall of the tubular vessel proximally as the cutter 4 advances distally, thereby pulling tissue into the cutter 4. The auger 6 pulls the wall of the tubular vessel intramurally; that is, by engaging the wall across its thickness using the flutes 13, to firmly and reliably engages the wall of the tubular vessel.

The cutter 4 is translated distally through the wall of the tubular vessel as the auger 6 holds a portion of the wall and pulls it proximally relative to the cutter 4. Thus, the cutter 4 cuts the tubular vessel from the outside while the auger 6 holds the wall of the tubular vessel. The auger 6 advances into the wall of the tubular vessel as the cutter 4 advances and cuts. The cutting action of the cutter 4 is both rotational and axial. The tissue of the tubular vessel may be strain rate sensitive, such as the tissue of the aorta. Strain rate sensitive tissue is easier to cut when the cutting is performed rapidly than when it is performed slowly. By actuating the auger 6 and the cutter 4 impulsively, they move rapidly such that the cutter 4 can better cut strain rate sensitive tissue, and enter the tissue quickly enough to minimize any effects of the tissue pulling outward from the opening in directions substantially perpendicular to the motion of the cutter 4. The pitch of the auger flutes 13 and the distance traveled by the cutter 4 during one rotation of the auger 6 are selected such that the auger 6 and cutter 4 cut a substantially cylindrical tissue plug from the wall of the tubular vessel. Alternately, the pitch of the auger flutes 13 and the distance traveled by the cutter 4 during one rotation of the auger 6 are selected such that the auger 6 and cutter 4 cut a substantially conical tissue plug from the wall of the tubular vessel. The conical tissue plug may be wider at its distal end or at its proximal end, depending on the selected pitch of the auger flutes 13 and the distance traveled by the cutter 4 during one rotation of the auger 6.

After the cutter 4 has penetrated the entire vessel wall, it has cut a tissue plug from that wall, and formed an opening corresponding to the former position of that tissue plug. The tissue plug is held firmly in the cutter 4 due to engagement with the auger flutes 13. The distal translation of the cutter 4 and auger 6 continues through a fixed distance greater than the thickness of the vessel wall, to ensure that the cutter 4 has completely penetrated the vessel wall. Thus, the cutter 4 and auger 6 may continue to advance for a short distance after the tissue plug has been cut out of the vessel wall. The cutter 4 and auger 6 are then retracted through the introducer tip 28. As they are retracted, they retract the tissue plug, leaving an opening in the wall of the tubular vessel.

Actuation of the auger 6 and the cutter 4 to remove a tissue plug from a vessel wall and create an opening therein may be performed in a number of different ways. Referring to FIGS. 11-12, in one exemplary embodiment, the cutter 4 and auger 6 are part of an integrated anastomosis tool 100. A single control on the integrated anastomosis tool 100 may be operated by the user to actuate the cutter 4 and the auger 6 and create an opening in the wall of the tubular vessel. This single control may be the knob 88, which is rotated through a preselected number of degrees in order to deploy the cutter 4 and auger 6, cut a tissue plug from the wall of the tubular vessel to form an opening in that wall, and retract the tissue plug out of the opening. A different control than the knob 88 may be provided, such as a lever, a slider, a button, or other control. The single control may be hand-driven, where force transmitted through the operator's hand drives at least part of the operation of the cutter 4 and auger 6, or may be powered, such that the operator simply presses a button or actuates a different control such that a powered mechanism such as a motor drives at least part of the operation of the cutter 4 and auger 6.

Referring to FIG. 11, the integrated anastomosis tool 100 is in the initial state; the auger 6 and the cutter 4 have not yet been deployed and the knob 88 is in an initial position. The user places the contact structure 110 against the wall of the tubular vessel in the location where the opening is to be made, without substantially deforming the tubular vessel. The user then begins to turn the knob 88. The stops 102 on the second driveshaft 52 are biased against the proximal surface 104 of the endplate 94 of the knob 88, as described above. The second driveshaft 52 does not substantially rotate upon rotation of the knob 88, because the registration features 64 connected to the second driveshaft 52 restrain the second driveshaft 52 against rotational movement, as described above. Initially, the slot 96 in the endplate 94 of the knob 88 is not aligned with the stops 102; instead, the stops 102 are in contact with the endplate 94 of the knob 88. At a preselected point in the angular travel of the knob 88, the slot 96 aligns with the stops 102, freeing the stops 102 to translate distally through the slot 102 and allowing the second driveshaft 52 to advance distally under the influence of the compression spring 106. Thus, the rotation of the knob 88 advances the second driveshaft 52 distally at a preselected point in the angular travel of the knob 88.

The distal advancement of the second driveshaft 52 translates the second gear 50 axially relative to the first gear 46. As described above, the first gear 46 is fixed, and engages the second gear 50 both before and after its advancement. As the second driveshaft 52 advances distally, the registration feature or features 64 advance distally relative to the structures or mechanisms that had previously restrained the second driveshaft 52 against rotation, freeing the registration feature or features 64. The second driveshaft 52 is then rotationally free, and begins to rotate driven by the energy stored within the spring 54. This stored energy is impulsively delivered, and in one embodiment causes the second gear 50 to rotate substantially three times. The gear ratio between the first gear 44 and the second gear 50 is chosen to produce the desired number of rotations of the second gear 50 upon release of stored energy from the spring 54. The second gear 50 rotates with the second driveshaft 52, causing the first gear 46 and the first driveshaft 26 to rotate in the opposite direction. Rotation of the first gear 46 also causes the first driveshaft 26 to advance distally, as described above. The actuator 24 transmits the rotary and translational motion of the first driveshaft 26 to the auger assembly 10 and the cutter 4.

The knob 88 is connected to the cam cylinder 70, such that rotation of the knob 88 rotates the cam cylinder 70. When the knob 88 is rotated to the position at which the second driveshaft 52 is allowed to advance distally, the first cam path 68 is positioned relative to the first cam follower 66 on the introducer tube 62 such that the first cam follower 66 and the introducer tube 62 are free to advance distally. The second cam follower 84 extending from the carriage 58 is prevented from moving substantially distally or proximally by the second cam path 86, which at this time is substantially perpendicular to the direction of motion of the introducer tube 62. Because the carriage 58 is held substantially fixed, the rotation of the threaded portion 72 of the first driveshaft 26 relative to the threaded passage 74 in the carriage 58 is converted to distal translation of the first driveshaft 26 as well. As the first driveshaft 26 advances distally, the fitting 78 on the first driveshaft 26 engages the seal housing 34 and impels it forward. The seal housing 34 is connected to the introducer tube 62, and is free to advance distally along with the introducer tube 62. Thus, the seal housing 34 and the components fixed to it, such as the introducer tip 28, advance distally. The integrated anastomosis tool 100 is then in the deployed state of FIG. 12.

Where the auger 6 is fluted, as is FIGS. 4-5, the cam cylinder 70 controls the motion of the auger 6 and cutter 4 in the same manner as described above. The portions of the cam paths 68, 86 allowing for translation are longer than described above, because the auger 6 and the cutter 4 are initially spaced apart from the vessel wall, and thus travel a further distance during their actuation. The auger 6 and the cutter 4 penetrate the intact vessel wall, cut a tissue plug to form an opening, and retract the tissue plug from the opening in the same manner as described above.

The user continues to rotate the knob 88. After the tissue plug has been cut from the wall of the tubular vessel, it is restrained within the cutter 4 as described above. The auger 6 and cutter 4 continue advancing until they have traveled the entire preselected distance extending distally from the contact structure 110. The auger 6 and the cutter 4 then are retracted. The second cam follower 84 travels within the second cam path 86 in the cam cylinder 70. As the cam cylinder 70 rotates as the knob 88 is turned, the second cam path 86 moves proximally relative to the second cam follower 84. That is, the second cam path 86 has an axial component, such that contact between the second cam path 86 and the second cam follower 84 translates the second cam follower proximally. Because the second cam follower 84 is connected to the carriage 58, the carriage 58 also is moved proximally, such that the auger 6 and the cutter 4, as well as the tissue plug they restrain, are removed from the opening in the wall of the tubular vessel through the introducer tip 28, which remains in the opening. The bushing 38 is retracted along with the auger assembly 10. Thus, an assembly that includes the cutter 4, the auger assembly 10 and the bushing 38 is retracted from the opening in the wall of the tubular vessel. The orientation of the auger 6 before this retraction defines a first axis.

As the bushing 38 moves proximally, the guide follower or followers on the bushing 38 are guided by the guides 35 within the seal housing 34. The guides 35 extend away from the first axis in order to move the bushing 38 away from the first axis as the bushing is moved proximally. That is, the auger 6 and the cutter 4 are moved off-axis during retraction. In one embodiment, moving proximally, each guide 35 slopes in a direction toward the opening 80. Thus, as the bushing 38 is retracted proximally, the guide followers encounter the upward-sloping guides 35, which cause the bushing 38 to move off the first axis to a second axis. The guide followers need not contact the guides 35 at all points during the retraction of the bushing. Indeed, the actuator 24 itself may be configured to bias the bushing 38, auger assembly 10 and cutter 4 away from the first axis. In this way, the auger 6, cutter 4 and the tissue plug that they retain, as well as the bushing 38, are moved off the first axis such that an anastomosis device can be deployed along the first axis through the introducer tube 62. Further, moving the auger 6 and cutter 4 off the first axis allows the tissue plug to be removed from the opening without being retracted through the graft vessel. By moving the tissue plug into a location within the seal housing 34, hemostasis is maintained.

Alternately, the guides 35 and guide followers need not be provided. For example, the guides 35 and guide followers may be unnecessary where the auger 6 and cutter 4 are not part of an integrated tool. As another example, the bushing 38, auger assembly 10 and cutter 4 may be retracted substantially along the first axis, and an anastomosis device is moved from another axis to the first axis for deployment. In such an example, the bushing 38 need not be moved off the first axis, and the guides 35 and guide followers are not required.

Figure 14:
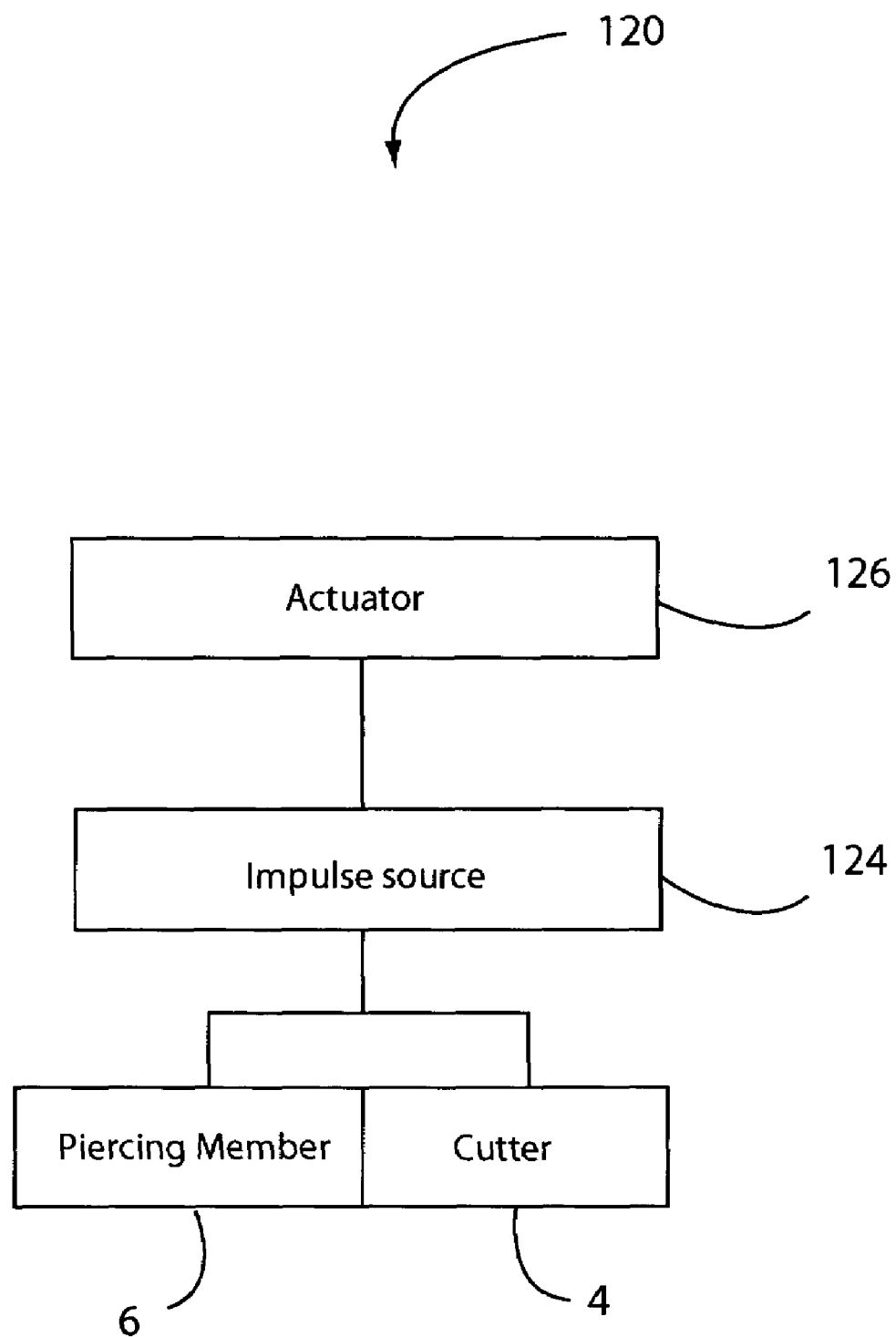
FIG. 14 is a schematic representation of an alternate embodiment of an assembly for creating an opening in the wall of a tubular vessel.

A stand-alone cutting tool 120 may be useful in creating an opening in the aorta of a patient, such as in preparation for a CABG procedure. However, the cutting tool 120 may be useful in creating an opening in other hollow or tubular tissue structures. Referring to FIG. 14, a stand-alone cutting tool 120 includes a cutter 4 and a piercing member 6, as described above. The piercing member 6 may be any embodiment of the auger 6 as described above, such as a fluted element, a needle or a spiked needle, or any other member configured to pierce the tissue of a vessel wall. The cutter 4 and/or piercing member 6 is operationally connected to the impulse source 124. Because the cutter 4 and piercing member 6 are fixed relative to one another with respect to translation, if the impulse source 124 delivers energy to one of them to cause translation, the connection therebetween causes the other to translate as well. The impulse source may be connected directly to the cutter 4 and piercing member 6, or may be connected indirectly to at least one of the cutter 4 and piercing member 6. The impulse source 124 is operationally connected to an actuator 126, which may be any suitable mechanism or structure such as a button or trigger. The actuator 126 may be a single control or a combination of different controls that are simultaneously operated. Manipulation of the actuator 126 causes the impulse source 124 to release energy to and provide an impulse to the cutter 4 and the piercing member 6. Advantageously, the actuator 126 may be operated by a single motion of the user.

Figure 15:
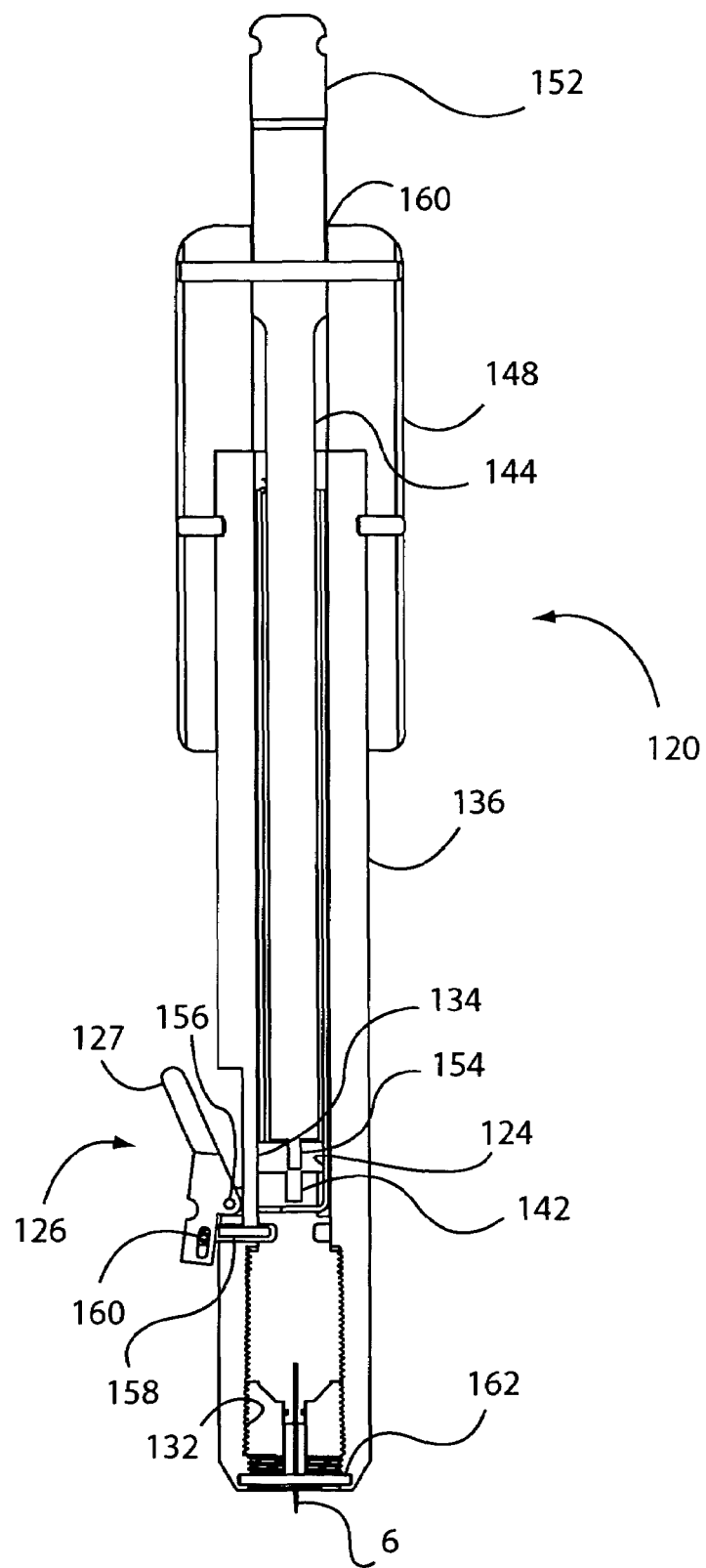
FIG. 15 is a side cross-section view of an alternate embodiment of an assembly for creating an opening in the wall of a tubular vessel, in a pre-firing state.
Figure 16:
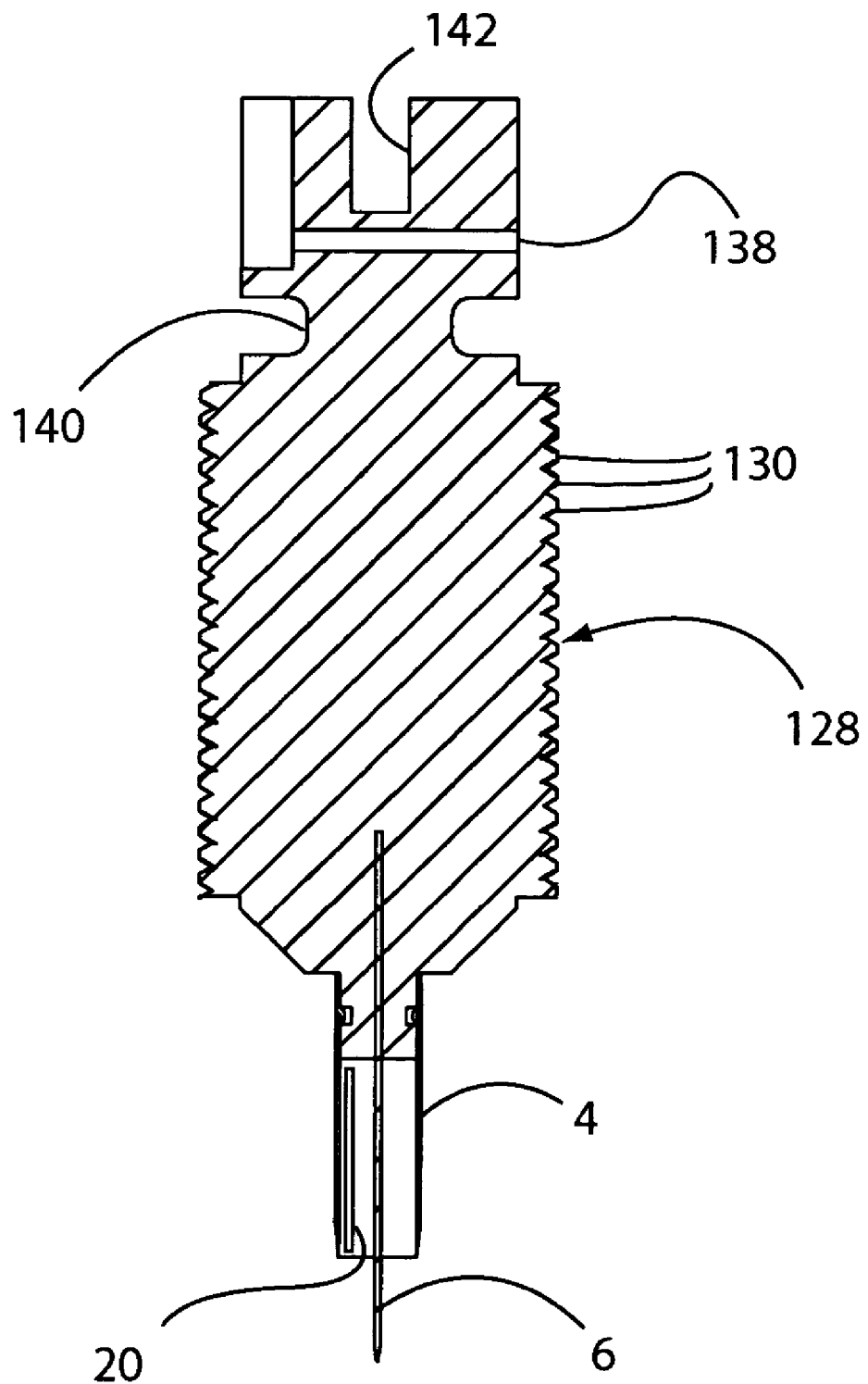
FIG. 16 is a side cross-section detail view of a piercing member and cutter forming part of the assembly of FIG. 15.

Referring also to FIGS. 15-16, an embodiment of a stand-alone cutting tool 120 includes the elements shown schematically in FIG. 14. The tool 120 includes a cutter 4 and an piercing member 6, each of which may be configured substantially as described above. The tool 120 may be configured to make more than one opening in the wall of one or more tubular tissue structures in a patient during a surgical procedure. Such a tool 120 may be disposable, resposable or reusable. Where the tool 120 is reusable, it is fabricated from materials that allow it to be sterilized and reused in a different patient at a later time. The cutter 4 may be configured to accumulate the tissue plugs from the different openings so that the user need not remove each plug from the cutter 4 before making the next opening. As an example, the cutter 4 may extend far enough in the longitudinal direction to accumulate a particular number of tissue plugs of a particular expected thickness. For example, where the cutter 4 is configured to make up to 5 separate openings in one or more tubular vessels, and the expected wall thickness of each vessel is at most 3 millimeters, the cutter 4 is at least 15 millimeters long, with an additional length added as a margin in the event that one or more vessels have a wall thickness over 3 millimeters. Where the cutter 4 is used to make multiple openings in at least one tubular vessel in a patient, the vent 20 in the cutter 4 is a slot 20 that extends longitudinally through the cutter 4, along at least part of its length. This slot 20 may be utilized instead of or in addition to a vent 20 at or proximal to the proximal end of the cutter 4, as described above. The longitudinal slot 20 allows for better venting where multiple tissue plugs are accumulated in the cutter 4, because the first tissue plug collected would block a vent 20 located in the proximal end of the cutter 4. The slot 20 extends along the cutter 4 a distance sufficient to vent the cutter 4 during the collection of each tissue plug. That is, as the tissue plugs accumulate, the slot 20 extends proximal and/or distal to the accumulated tissue plugs, such that air can be vented between the most proximal tissue plug and the proximal end of the cutter 4 or between the most distal accumulated tissue plug and the wall of a tubular tissue structure, or both. Alternately, the slot 20 is nonlinear, but still extends across a longitudinal distance on the cutter 4 sufficiently to vent the cutter 4 during the collection of each tissue plug.

The cutter 4 and the piercing member 6 are connected to a header 128 in any appropriate manner. For example, the cutter 4 may be dimpled to the header 128, and the header 128 may be molded around the proximal end of the piercing member 6. Alternately, the cutter 4, piercing member 6 and header 128 may be formed as a single unit. The cutter 4 and piercing member 6 are connected to the header 128 such that both the cutter 4 and the piercing member 6 are fixed translationally to one another. That is, the piercing member 6 and the cutter 4 are configured to translate together at the same rate in the axial direction, that axial direction being the direction along the longitudinal centerline of the piercing member 6. The cutter 4 and piercing member 6 may be free to rotate relative to one another. The cutter 4 and the piercing member 6 may also be connected to the header 128 such that they are fixed rotationally to one another, such that they both advance axially and rotate together. The header 128 may be a screw, and may be molded, machined or otherwise fabricated. The screw is threaded, such that its threads 130 are configured to engage corresponding threads 132 in the inner wall 134 of the body 136 of the tool 120. The pitch of the threads 130, 132 is substantially the same, and is selected to control the longitudinal motion of the cutter 4 and piercing member 6 as described below. Alternately, the header 128 may be configured differently. The header 128 may include a connection feature 138, such as a tunnel, aperture or trough, for connection to the impulse source 124. The header 128 may also include an actuator engagement feature 140, such as an aperture or trough, configured to engage the actuator 126. The engagement feature 140 may be formed in any suitable manner. As one example, the engagement feature 140 may be a circumferential trough or depression oriented substantially transverse to the longitudinal centerline of the header 128. As another example, the engagement feature 140 may be a slot or aperture located at a particular angular position on the header 128. The header 128 may also include a receiver 142, such as an aperture or trough, configured to engage a reload shaft 144 as described in greater detail below.

The impulse source 124 may be any suitable source of impulsive force, as described above. As one example, the impulse source 124 is a torsion spring 124 located within the body 136 of the tool 120. The distal end of the torsion spring 124, and/or a different part of the torsion spring 124, is connected to the connection feature 138 in any suitable manner. As one example, the torsion spring 124 is a coiled wire, and the wire at the distal end of the torsion spring 124 curves or loops through the connection feature 138 of the header 128. The proximal end of the compression spring, and/or a different part of the torsion spring 124 proximal to the connection feature 138, is connected to the body 136 of the tool 120 or other portion of the tool 120. As an example, where the torsion spring 124 is a coiled wire, the wire at the proximal end of the torsion spring 124 is molded into or otherwise secured to the body 136 of the tool 120. The proximal end of the torsion spring 124 is substantially fixed relative to the body 136 of the tool 120, while the distal end of the torsion spring 124 is substantially free to move along with the header 128.

The tool 120 includes a cap 148 that is connected to or formed into the distal end of the body 136. An aperture 150 is defined through the cap 148, where that aperture 150 is substantially oriented along the longitudinal centerline of the body 136. The reload shaft 144 extends through the aperture 150. A knob 152 may be connected to or formed into the proximal end of the reload shaft 144, in order to prevent the reload shaft 144 from passing completely through the aperture 150 into the body 136 and/or to facilitate rotation of the reload shaft 144. The knob 152 may be configured to facilitate gripping and rotating it; for example, the knob 152 may be knurled, may have a large diameter compared to the body 136, may have a rubberized or frictional gripping surface, or may be configured otherwise. The reload shaft 144 extends through the center of the impulse source 124 to minimize or prevent interference between them. Alternately, the reload shaft 144 is positioned differently relative to the impulse source 124. A post 154 extends proximally from the proximal end of the reload shaft 144, and is positioned to be selectively engageable with the receiver 142. The post 154 and the receiver 142 are sized and shaped such that the receiver 142 can receive the post 154. The post 154 can be positioned in any appropriate manner. As one example, the post 154 is substantially aligned with the longitudinal centerline of the reload shaft 144. The post 154 is shaped to have a rectangular, square, polygonal or other cross-section to engage the receiver 142 and rotate the header 128, as described in greater detail below. As another example, the post 154 is substantially parallel to and offset from the longitudinal centerline of the reload shaft 144 by substantially the same amount as the receiver 142 in the header 128. Where the post 154 is offset from the longitudinal centerline of the reload shaft 144, the post 154 may be cylindrical or otherwise shaped.

The actuator 126 is connected to the body 136 of the tool 120 in any appropriate manner. The actuator 126 includes a trigger 127 connected to a restraint 158. The trigger 127 may be a lever, a button, a rod, a switch or any other appropriate structure or mechanism that can be engaged by a user. The trigger 127 may be pivotally mounted to an axle 156 that is connected to or formed into the body 136 of the tool 120. The axle 156 is oriented substantially transverse to the longitudinal centerline of the body 136, such that at least a portion of the trigger 127 can rock downward toward the body 136 of the tool 120 upon actuation. Alternately, the axle 156 is oriented differently, such that the trigger 127 is movable in a different direction. The portion of the trigger 127 proximal to the axle 156 is movable toward the body 136 of the tool 120 when pressure is applied to it in the direction of the body 136, such as by the finger of a user. The portion of the trigger 127 distal to the axle 156 is connected to the restraint 158. A pin 160 substantially parallel to the axle 156 may link the trigger 127 to the restraint 158. Alternately, the trigger 127 and the restraint 158 are connected in a different manner. Further, the trigger 127 may be configured to move in the opposite direction, such that its distal end is movable away from the body 136 of the tool 120.

The actuator 126 is movable between a first position and a second position. In the first position, the restraint 158 extends through an aperture (not shown) in the body 136 of the tool 120, into the actuator engagement feature 140 of the header 128. The presence of at least a portion of the restraint 158 in the actuator engagement feature 140 restrains the header 128 against distal motion. The portion of the trigger 127 proximal to the axle 160 is away from the body 136 of the tool 120. In the second position, the actuator 126 has moved the restraint 158 out of the actuator engagement feature 140, freeing the header 128, and the cutter 4 and piercing member 6, to move distally. The portion of the trigger 127 proximal to the axle 160 is closer to the body 136 of the tool 120.

At or near the distal end of the body 136, and at or near the distal end of the threads 132 in the body 136, at least one stop 162 is connected to the body 136. The stop or stops 136 are configured to stop the header 128 at the conclusion of its travel, as described below, such that the header 128 does not become disengaged from the body 136. Additionally, the distal end of the body 136 may include an introducer tip 28 as described above.

The operation of the stand-alone tool 120 will now be described. Initially, the tool 120 is in a first, pre-firing state, in which the tool 120 is ready for use in creating an opening in the wall of a tubular tissue structure. In the pre-firing state, the header 128, cutter 4 and piercing member 6 are in a first position, as shown in FIG. 15. In the pre-firing state, the impulse source 124 may store a selected amount of energy, directed distally toward the header 128. If so, the engagement between the restraint 158 and the engagement feature 140 restrains the holder 128 substantially against distal motion, and additionally ensures that the energy stored in the impulse source 124 remains in potential form and is not converted to kinetic energy. In the pre-firing state, the cutter 4 and the piercing member 6 are positioned at least partially within the body 136 of the tool 120, and do not extend out of the introducer tip 28 (if used) or the distal end of the body 136. When the tool 120 is in the pre-firing state, the actuator 126 is also in its first position. The end of the trigger 127 proximal to the axle 156 is spaced away from the body 136 of the tool 120. Finally, when the tool 120 is in the pre-firing state, the reload shaft 144 is positioned relative to the header 128 such that the post 154 is at least partially within the receiver 142. The presence of at least a portion of the post 154 within the receiver 142 substantially prevents rotation of the header 128, even if the restraint 158 were to be removed from the engagement feature 140; because the reload shaft 144 may be restrained against rotation prior to firing, or may be configured such that it is not capable of rotation relative to the body 136 of the tool 120. In this way, the post 154 acts as a safety or lockout.

The user moves the tool 120 into position relative to the tubular tissue vessel in which an opening is to be made. No previous incision, cut, or hole need be present in the tissue. The distal end of the tool 120 is placed against the outer wall of the tubular tissue vessel. The reload shaft 144 is then moved proximally, moving the post 154 out of engagement with the receiver 142. Where the knob 152 is provided, the user may grasp the knob 152 and pull it proximally in order to move the reload shaft 144. The reload shaft 144 may be moved in another way, if desired. The tool 120 is then ready for firing.

Next, the user depresses the trigger 127. The proximal end of the trigger 127 moves toward the body 136, and the distal end of the trigger 127 moves away from the body 136 as the trigger 127 rotates about the axle 156. As the distal end of the trigger 127 moves away from the body 136, it exerts a force on the restraint 158 in a direction away from the body 136, pulling the restraint 158 out of the engagement feature 140.

When the restraint 158 is disengaged from the engagement feature 140, the header 128 is free to move. The impulse source 124 delivers energy to the header 128, causing it to rotate. In this way, the actuator 126 is operationally connected to the impulse source 124; operation of the actuator 126 allows the impulse source 124 to deliver energy to the cutter 4 and piercing member 6. The threads 130 of the header 128 advance along the threads 132 in the body 136 of the tool 136. The threads 130, 132 add a translational component to the motion of the header 128. That is, the engagement between the threads 130, 132 adds a component of motion in the longitudinal direction to the rotational motion of the header 128. A portion of the impulse delivered to the header 128 is thus converted to rotation of the header 128, cutter 4 and piercing member 6, and a portion of that impulse is converted to translation of the header 128, cutter 4 and piercing member 6.

As the header 128 advances, the piercing member 6 begins to penetrate the tissue of the tubular tissue structure, followed by the distal edge of the cutter 4. The piercing member 6 and cutter 4 advance at the same rate, which is chosen to facilitate their entry into tissue. The piercing member 6 and cutter 4 are advanced into the wall of the tissue structure fast enough such that the blood or other fluid in the tubular structure acts as a solid and supports the wall of the tubular structure against the advance of the piercing member 6 and cutter 4. That is, the piercing member 6 and cutter 4 advance into the wall of the tissue structure fast enough that the fluid within substantially does not have time to move in response to the motion of the piercing member 6 and cutter 4, such that the fluid acts as if it were a solid. Experiments have shown that the rate at which the piercing member 6 and cutter 4 should advance to accomplish this effect is substantially 0.8-1.4 m/sec. Similarly, the duration over which the header 128 is advanced is advantageously less than one second; as described above, that duration may be substantially 0.05 seconds. The impulse source 124 may be configured to deliver at least some energy to the header 128 over a longer time, in a configuration in which the stop 162 acts to stop motion of the cutter 4 and piercing member 6 at a particular proximal-most location. The rotary speed of the cutter 4 is not as critical as the linear speed of the cutter 4 when aortic tissue is to be cut. A rotary speed of the cutter 4 corresponding to a thread pitch of 24 threads per inch has been shown by experiment to provide good results. Where the impulse source 124 is a torsion spring 124, the torsion spring is configured to wind during deployment. In this way, the length of the torsion spring 124 increases during firing, in order to correspond to the distal motion of the header 128. The header 128 may be configured to continue to rotate after encountering the stop 162, thereby dissipating any remaining energy stored in the impulse source 124 and/or associated with the momentum of the header 128, cutter 4 and piercing member 6. That is, the header 128 may be allowed to idle rotationally after it has completed its distal translation.

Alternately, where energy is not stored in the impulse source 124, the depression of the trigger 127 and/or the disengagement of the restraint 158 from the engagement feature 140 causes, or is performed in parallel with an action that causes, energy to be delivered to the impulse source 124. For example, where the impulse source 124 is a DC motor or solenoid, an electrical switch may be connected to or included in the trigger 127, such that motion of the trigger 127 up to or past a particular point causes DC current to be provided to that DC motor or solenoid.

As the cutter 4 advances into the wall of the tubular vessel, it cuts a tissue plug therefrom. That tissue plug that it has cut from that wall is located within and held within the cutter 4, as described above. As one example, one or more capture features 146 defined in the cutter 4 are oriented proximally, such that the tissue plug can move proximally relative to the capture feature or features 146, but such that the tissue plug is engaged by one or more capture features 146 should it move distally. As another example, friction between the cutter 4 and the piercing member 6 holds the tissue plug in place. The vent 20 allows that tissue plug to be received into the cutter 4 without being opposed by the presence of air between the tissue plug and the proximal end of the cutter 4. The header 128 advances until it encounters the stop 162 and/or until the impulse source 124 ceases to deliver energy to the header 128. Referring also to FIG. 17, the tool 120 is now in a post-firing state. An opening has been created in the wall of the target vessel, and the tool 120 may then be removed from that opening.

If the tool 120 is to be reused, the user may move the reload shaft 144 proximally, rotating it as needed to place the post 154 back into engagement with the receiver 142. The reload shaft 144 is then rotated by the user, such as by turning the knob 152. The tissue plug captured in the cutter 4 may be allowed to remain in the cutter 4, where the cutter 4 is long enough or otherwise configured to have sufficient volume therein to accommodate multiple tissue plugs as described above. Alternately, the tool 120 is configured to remove the tissue plug from the cutter 4 automatically as the tool 120 is returned to the pre-firing state. Where the post 154 is substantially aligned with the longitudinal centerline of the reload shaft 144, it may be rectangular, square, or any other shape that when in engagement with the receiver 142 allows the reload shaft 144 to rotate the header 128. That is, the post 154 and the receiver 142 are shaped to allow transmission of torque therebetween. Where the receiver 142 is offset from the longitudinal centerline of the header 128, which is substantially coincident with the longitudinal centerline of the reload shaft 144. Thus, as the reload shaft 144 is rotated, the post 154 in engagement with the receiver 142 is rotated about the longitudinal centerline of the header 128, causing the header 128 to rotate and move proximally.

As the reload shaft 144 is rotated, the motion of the header 128 may deliver energy to the impulse source 124. For example, where the impulse source 124 is a torsion spring 124, the motion of the header 128 unwinds the torsion spring 124, imparting potential energy to it. As the torsion spring 124 unwinds, its diameter increases, and it becomes shorter, consistent with the motion of the header 128 in the proximal direction. Alternately, the impulse source 124 includes a battery, gas cartridge or other mechanism or structure that is capable of storing enough energy to fire the piercing member 6 and cutter 4 multiple times. If so, the motion of the header 128 back to the pre-firing position need not deliver energy to the impulse source 124. Alternately, the impulse source 124 does not store energy; for example, if the impulse source 124 is a DC motor. If so, the motion of the header 128 back to the pre-firing position need not deliver energy to the impulse source 124. The reload shaft 144 is rotated until the restraint 158 is movable back into the engagement feature 140 of the header 128. The trigger 127 is moved back to the first position, moving the restraint 158 back into the engagement feature 140. Optionally, a stop (not shown) is provided at the proximal end of the threads 132 in the body 136. The stop may be particularly useful where the engagement feature 140 is not circumferential, and thus needs to be angularly aligned with the restraint 158 in order for the restraint 158 to engage it.

The tool 120 is then ready to be fired again as described above. The tool 120 can be reused as many times in the same patient as the cutter 4 can accommodate. That is, the cutter 4 is designed to capture a particular number of tissue plugs, and the tool 120 can be used to create an equivalent number of openings in tubular structures within the same patient. Alternately, if the cutter 4 is designed to hold one or more tissue plugs, the user can remove one or more tissue plugs from the cutter 4 when it has reached its capacity of holding tissue plugs, and continue making openings in tubular tissue structures.

While the invention has been described in detail, it will be apparent to one skilled in the art that various changes and modifications can be made and equivalents employed, without departing from the present invention. Although embodiments have been described above with regard to a CABG procedure, the apparatus and method described above are not limited to use in such a procedure. Further, the cutter and auger disclosed above may be utilized to create openings in tubular vessels and bodily structures other than blood vessels. It is to be understood that the invention is not limited to the details of construction and/or the arrangements of components set forth in the above description or illustrated in the drawings. Therefore, the invention is not to be restricted or limited except in accordance with the following claims and their legal equivalents.

What is claimed is:

1. A method for making an opening in the intact wall of an aorta, comprising:
   providing a cutter and a piercing member positioned within said cutter; wherein said piercing member and said cutter are configured to translate together;
   advancing said cutter and said piercing member at a speed between substantially 0.8 meters per second and substantially 1.4 meters per second; and
   rotating said cutter.

2. The method of claim 1, wherein said advancing is impulsive.

3. The method of claim 1, wherein said advancing occurs for a duration less than one second.

4. A method for making an incision in and removing tissue from a vessel wall, comprising:
   providing a cutter and a piercing member positioned within said cutter, movable between a pre-firing state and a post-firing state;
   placing said cutter and said piercing member in proximity to the vessel;
   imparting an impulse to said cutter and said piercing member when in said pre-firing state; and
   converting said impulse to rotary motion and to translational motion through the vessel wall.

5. The method of claim 4, further comprising moving said cutter and said piercing member from said post-firing state to said pre-firing state.

6. The method of claim 4, wherein the duration of said impulse is less than one second.

7. The method of claim 4, wherein fluid is present within the vessel, and wherein said impulse is exerted over a time short enough such that the fluid within the vessel behaves as an incompressible fluid upon contact between said cutter and the vessel wall.

8. The method of claim 4, wherein said impulse source is a torsion spring, wherein said imparting further comprises winding said torsion spring as said cutter and said piercing member move from said pre-firing state to said post-firing state.

9. The method of claim 4, wherein said impulse source is a torsion spring, wherein said imparting further comprises unwinding said torsion spring as said cutter and said piercing member move from said post-firing state to said pre-firing state.

* * * * *